US010739360B2

(12) United States Patent
Suzuki et al.

(10) Patent No.: US 10,739,360 B2
(45) Date of Patent: Aug. 11, 2020

(54) METHOD FOR ANALYZING BLOOD SPECIMEN, AND ANALYZER

(71) Applicants: SYSMEX CORPORATION, Kobe-shi, Hyogo (JP); NATIONAL UNIVERSITY CORPORATION NAGOYA UNIVERSITY, Nagoya-shi, Aichi (JP)

(72) Inventors: Atsuo Suzuki, Nagoya (JP); Tadashi Matsushita, Nagoya (JP); Sho Shinohara, Kobe (JP); Nobuo Arai, Kobe (JP)

(73) Assignees: NATIONAL UNIVERSITY CORPORATION NAGOYA UNIVERSITY, Nagoya-Shi, Aichi (JP); SYSMEX CORPORATION, Kobe-Shi, Hyogo (JP)

( * ) Notice: Subject to any disclaimer, the term of this patent is extended or adjusted under 35 U.S.C. 154(b) by 113 days.

(21) Appl. No.: 15/957,308

(22) Filed: Apr. 19, 2018

(65) Prior Publication Data
US 2018/0306820 A1   Oct. 25, 2018

(30) Foreign Application Priority Data
Apr. 24, 2017 (JP) ................................. 2017-085329

(51) Int. Cl.
| G01N 33/86 | (2006.01) |
| G01N 33/49 | (2006.01) |
| G01N 21/27 | (2006.01) |
| G01N 21/82 | (2006.01) |

(52) U.S. Cl.
CPC .......... *G01N 33/86* (2013.01); *G01N 21/272* (2013.01); *G01N 21/82* (2013.01);
(Continued)

(58) Field of Classification Search
CPC .......... G01N 2021/825; G01N 21/272; G01N 21/82; G01N 2333/75; G01N 2333/94; G01N 33/49; G01N 33/4905; G01N 33/86
(Continued)

(56) References Cited

U.S. PATENT DOCUMENTS 4,047,890 A * 9/1977 Eichelberger .......... G01N 21/82
 436/69
5,851,836 A * 12/1998 Enomoto ............... G01N 33/86
 436/69
(Continued)

FOREIGN PATENT DOCUMENTS

| CA | 1062501 | 9/1979 |
| EP | 0587398 | 3/1994 |
(Continued)

OTHER PUBLICATIONS

Suzuki et al. Thrombosis Research, vol. 174, pp. 98-103, Dec. 18, 2018.*
(Continued)

*Primary Examiner* — Maureen Wallenhorst
(74) *Attorney, Agent, or Firm* — Brinks Gilson & Lione

(57) ABSTRACT

Disclosed is an analyzing method, for analyzing a blood specimen, which includes: mixing a blood specimen and a thrombin-containing reagent to coagulate the blood specimen, and obtaining a coagulation waveform; obtaining a value of a parameter concerning differentiation of the coagulation waveform, based on the coagulation waveform; and obtaining information concerning an amount of antigen of fibrinogen based on the obtained value of the parameter.

10 Claims, 18 Drawing Sheets

(51) Int. Cl.
(52) U.S. Cl.
CPC ... *G01N 33/4905* (2013.01); *G01N 2021/825* (2013.01); *G01N 2333/75* (2013.01); *G01N 2333/94* (2013.01)
(58) Field of Classification Search
USPC .............. 436/63, 69, 164; 435/13; 422/73; 73/64.41, 64.43; 600/369
See application file for complete search history.

(56) References Cited

U.S. PATENT DOCUMENTS

| | | | |
|---|---|---|---|
| 6,165,795 A * | 12/2000 | Mize ................. | G01N 33/4905 356/39 |
| 2016/0291042 A1* | 10/2016 | Kumano ............ | G01N 33/4905 |
| 2017/0363650 A1* | 12/2017 | Van Ooijen ........... | G01N 33/86 |

FOREIGN PATENT DOCUMENTS

| | | |
|---|---|---|
| EP | 3076173 | 10/2016 |
| EP | 3225998 A1 | 10/2017 |
| JP | 2007-107889 A | 4/2007 |
| WO | WO 2016/097234 | 6/2016 |
| WO | WO 2017/167706 A1 | 10/2017 |

OTHER PUBLICATIONS

Jacquemin et al., "The Amplitude of Coagulation Curves from Thrombin Time Tests Allows Dysfibrinogenemia Caused by the Common Mutation FGG-Arg301 to be Distinguished from Hypofibrinogenemia," International Journal of Laboratory Hematology, John Wiley & Sons Ltd., 2017, vol. 39, No. 3, 7 pages.
Office Action in Europe Application No. 18167717.0, dated Jul. 25, 2019, 8 pages.
Extended European Search Report in Europe Application No. 18167717.0, dated Jun. 6, 2018, 8 pages.
Miesbach et al., "Comparison of the fibrinogen Clauss assay and the fibrinogen PT derived method in patients with dysfibrinogenemia" Thrombosis Research, vol. 126, No. 6, Oct. 13, 2010, pp. e428-e433.

* cited by examiner

METHOD FOR ANALYZING BLOOD SPECIMEN, AND ANALYZER

RELATED APPLICATIONS

This application claims priority from prior Japanese Patent Application No. 2017-085329, filed on Apr. 24, 2017, entitled "METHOD FOR ANALYZING BLOOD SPECIMEN, ANALYZER, AND COMPUTER PROGRAM", the entire content of which is incorporated herein by reference.

FIELD OF THE INVENTION

The present invention relates to a method for analyzing a blood specimen. The present invention also relates to a blood specimen analyzer and a computer program.

BACKGROUND

Fibrinogen is also called coagulation factor I, and is associated with forming of a fibrin clot in vivo. Fibrinogen becomes fibrin by the action of thrombin. The fibrin becomes firmly stabilized fibrin by the action of activated coagulation factor XIII, to form a fibrin clot. Fibrinogen is not only important for diagnosis and prognostication of hemorrhagic diseases, but also is an important index as a risk factor of thrombosis.

Examples of a fibrinogen measurement method include a thrombin time method (Clauss method), a salt precipitation method, immunonephelometry, and the like. In view of convenience and cost, the Clauss method is widespread. A thrombin-containing reagent and a kit for measuring fibrinogen, which are suitable for the Clauss method, are commercially available. The Clauss method is a method in which activity of fibrinogen is measured according to a time, in which fibrinogen is converted to fibrin by a predetermined amount of thrombin, depending on fibrinogen concentration. In the Clauss method, by generating a calibration curve based on a result of measuring of fibrinogen standard solution the concentration of which is known, an active concentration of fibrinogen in a blood specimen can be also obtained.

The Clauss method is preferably used because the Clauss method is applicable to an automatic blood coagulation measurement device. For example, Japanese Laid-open Patent Publication No. 2007-107889 discloses measuring a coagulation time by using a blood specimen analyzer, and obtaining a concentration of fibrinogen. In Japanese Laid-open Patent Publication No. 2007-107889, the concentration of fibrinogen is an active concentration of fibrinogen.

The active concentration of fibrinogen obtained by the Clauss method is a fibrinogen concentration obtained in the case of a function of the fibrinogen in a blood specimen being assumed to be normal. Therefore, when the active concentration is low, whether the cause is reduction of an amount of fibrinogen as protein (amount of antigen) or abnormal activity of the fibrinogen, needs to be separately confirmed. This is because a suspected disease is different depending on the cause of reduction of the active concentration. When the cause is reduction of an amount of antigen of fibrinogen, the suspected disease is fibrinogen deficiency or hypofibrinogenemia. When the cause is abnormal activity of fibrinogen, the suspected disease is fibrinogen disorder.

To date, an amount of antigen of fibrinogen is measured by immunological measurement such as a latex agglutination method. However, depending on facilities, although coagulation time is measured by the Clauss method, immunological measurement may not be performed. Therefore, means capable of obtaining information concerning an amount of antigen of fibrinogen, based on measurement of the coagulation time of a blood specimen having thrombin added thereto, is expected to be developed.

The inventors have found that a value of a parameter obtained by differentiating a coagulation waveform in a thrombin time method (Clauss method) and a total reaction time obtained from the coagulation waveform are well correlated with an amount of antigen of fibrinogen measured in a latex agglutination method, and have completed the present invention.

SUMMARY OF THE INVENTION

The scope of the present invention is defined solely by the appended claims, and is not affected to any degree by the statements within this summary.

A first mode of the present invention is an analyzing method for analyzing a blood specimen, and the analyzing method includes: mixing a blood specimen and a thrombin-containing reagent to coagulate the blood specimen, and obtaining a coagulation waveform; obtaining a value of a parameter concerning differentiation of the coagulation waveform, based on the coagulation waveform; and obtaining information concerning an amount of antigen of fibrinogen based on the obtained value of the parameter.

A second mode of the present invention is an analyzing method for analyzing a blood specimen, and the analyzing method includes: mixing a blood specimen and a thrombin-containing reagent to coagulate the blood specimen, and obtaining a coagulation waveform; obtaining, based on the coagulation waveform, a value of a parameter concerning differentiation of the coagulation waveform, and a coagulation time; and obtaining information concerning a function of fibrinogen based on the obtained value of the parameter and the obtained coagulation time.

A third mode of the present invention is a blood specimen analyzer that includes: a measurement unit configured to prepare a measurement sample that contains a blood specimen and a thrombin-containing reagent, and obtain a coagulation waveform from the prepared measurement sample; and an information obtaining unit configured to obtain information concerning an amount of antigen of fibrinogen based on the coagulation waveform, and the information obtaining unit obtains a value of a parameter concerning differentiation of the coagulation waveform based on the coagulation waveform obtained by the measurement unit, and obtains the information concerning an amount of antigen of fibrinogen based on the obtained value of the parameter.

A fourth mode of the present invention is a blood specimen analyzer that includes: a measurement unit configured to prepare a measurement sample that contains a blood specimen and a thrombin-containing reagent, and obtain a coagulation waveform from the prepared measurement sample; and an information obtaining unit configured to obtain information concerning a function of fibrinogen based on the coagulation waveform, and the information obtaining unit obtains a value of a parameter concerning differentiation of the coagulation waveform, and a coagulation time, based on the coagulation waveform obtained by the measurement unit, and obtains the information concerning a function of fibrinogen based on the obtained value of the parameter and the obtained coagulation time.

A fifth mode of the present invention is a computer program, for analyzing a blood specimen, stored in a computer-readable medium, and the computer program causes the computer to execute: obtaining a value of a parameter concerning differentiation of a coagulation waveform based on the coagulation waveform obtained from a measurement sample that contains a blood specimen and a thrombin-containing reagent; and obtaining information concerning an amount of antigen of fibrinogen based on the obtained value of the parameter.

A sixth mode of the present invention is a computer program, for analyzing a blood specimen, stored in a computer-readable medium, and the computer program causes the computer to execute: obtaining a value of a parameter concerning differentiation of a coagulation waveform, and a coagulation time, based on the coagulation waveform obtained from a measurement sample that contains a blood specimen and a thrombin-containing reagent; and obtaining information concerning a function of fibrinogen based on the obtained value of the parameter and the obtained coagulation time.

A seventh mode of the present invention is an analyzing method, for analyzing a blood specimen, which includes: mixing a blood specimen and a thrombin-containing reagent to coagulate the blood specimen, and obtaining a coagulation waveform; obtaining a total reaction time up to a time when a measurement value of the coagulation waveform no longer changes, based on the coagulation waveform; and obtaining information concerning an amount of antigen of fibrinogen based on the total reaction time.

An eighth mode of the present invention is an analyzing method, for analyzing a blood specimen, which includes: mixing a blood specimen and a thrombin-containing reagent to coagulate the blood specimen, and obtaining a coagulation waveform; obtaining a coagulation time and a total reaction time up to a time when a measurement value of the coagulation waveform no longer changes, based on the coagulation waveform; and obtaining information concerning a function of fibrinogen based on the total reaction time and the coagulation time.

DETAILED DESCRIPTION OF THE PREFERRED EMBODIMENTS

Figure 1:
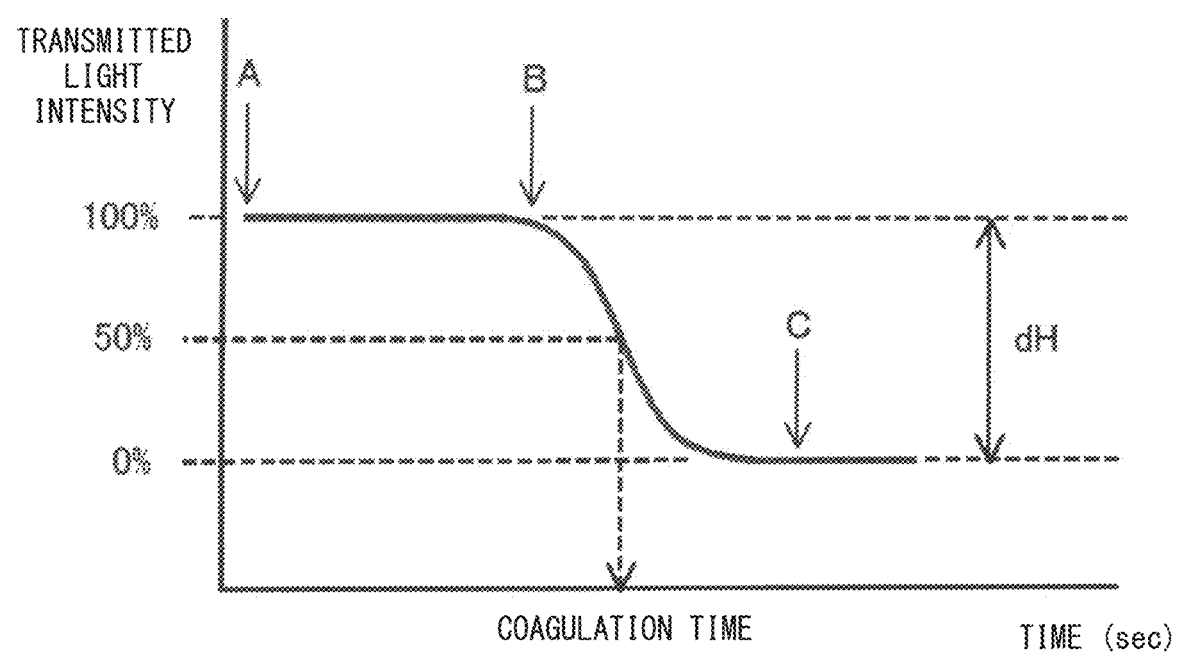
FIG. 1 illustrates an example of a coagulation waveform obtained by measuring a transmitted light intensity of a measurement sample that contains normal plasma and a thrombin-containing reagent.

[1. Method for Analyzing Blood Specimen for Obtaining Information Concerning an Amount of Antigen of Fibrinogen]

As described above, the inventors have found that a value of a parameter concerning differentiation of a coagulation waveform, and a total reaction time are well correlated with an amount of antigen of fibrinogen measured by the latex agglutination method. Hereinafter, a first mode in which a value of a parameter concerning differentiation of a coagulation waveform is used, and a seventh mode in which a total reaction time is used, will be described.

In a method for analyzing a blood specimen according to each of the first mode and the seventh mode, firstly, a blood specimen and a thrombin-containing reagent are mixed, to coagulate the blood specimen, and a coagulation waveform is obtained.

Examples of the blood specimen include whole blood and plasma. The blood specimen is preferably plasma. To the blood specimen, a known anticoagulant agent usually used in a coagulation test may be added. Examples of such an anticoagulant agent include trisodium citrate. The blood specimen may be diluted by using an appropriate buffer solution such as Owren's Veronal Buffer as necessary. Before a thrombin-containing reagent is added, the blood specimen may be heated in advance to a temperature (for example, not lower than 36° C. and not higher than 38° C.) that is suitable for coagulation reaction.

Some of the blood specimens may include a large amount of chyle, bilirubin, and the like. Furthermore, a large amount of hemoglobin may be included in the blood specimen due to hemolysis. Substances such as chyle, bilirubin, and hemoglobin are known as interference substances that influence optical measurement of blood coagulation. However, the inventors have found that a parameter concerning differentiation of a coagulation waveform and a total reaction time are less likely to be influenced by the interference substance. In particular, a value of a parameter concerning differentiation of a coagulation waveform is rarely influenced by the interference substance. Therefore, in the present embodiment, the blood specimen may contain the interference substance.

The thrombin-containing reagent may be a reagent that contains thrombin and is used for a case where the thrombin time method (Clauss method) is a measurement principle. The thrombin-containing reagent may be a freeze-dried product. However, the thrombin-containing reagent is preferably a liquid reagent when used. The thrombin may be a natural thrombin derived from a mammal such as a bovine, or may be a recombinant thrombin. In the present embodiment, as the thrombin-containing reagent, a commercially available thrombin reagent or a kit for measuring fibrinogen based on a thrombin time method may be used. Examples of such a reagent and a kit include Thrombocheck Fib (SYSMEX CORPORATION) and MultifibrenU (Siemens). The thrombin-containing reagent may be heated in advance to a temperature (for example, not lower than 36° C. and not higher than 38° C.) that is suitable for coagulation reaction before used.

The coagulation waveform obtained in the present embodiment is a coagulation waveform according to the thrombin time method. The blood coagulation reaction by thrombin reflects the coagulation phase 3, and is different from intrinsic coagulation and extrinsic coagulation. Therefore, in the field of blood test, the coagulation waveform obtained in the present embodiment is different from a coagulation waveform based on a measurement principle (for example, prothrombin time, activated partial thromboplastin time) other than the thrombin time method.

When the thrombin-containing reagent is added to the blood specimen, coagulation starts. Therefore, simultaneously when the thrombin-containing reagent is added, the coagulation waveform is measured. Hereinafter, a mixture of a blood specimen and a thrombin-containing reagent is referred to as a "measurement sample". In the description herein, the coagulation waveform represents a waveform that is generated according to progress of coagulation of a blood specimen, and that represents a temporal change of a value that indicates optical or physical characteristics of the specimen. In the present embodiment, the coagulation waveform may be obtained by an optical measurement method or a physical measurement method. Examples of the optical measurement method include a method in which light is applied to a measurement sample to obtain optical information such as a transmitted light intensity. Examples of the physical measurement method include a method in which a steel ball is used to obtain physical information such as viscosity of the measurement sample. The measurement may be performed by an automatic blood coagulation measurement device. For example, CS-Series of the automatic blood coagulation measurement devices (SYSMEX CORPORATION) can measure optical information such as a transmitted light intensity, and STA Compact of the automatic blood coagulation and fibrinolysis measurement device (Roche Diagnostics K.K.) can measure physical information such as viscosity.

A measurement condition is not particularly limited. The optical information or physical information is preferably obtained continuously or intermittently from a time when a measurement sample is prepared (specifically, a time when the thrombin-containing reagent is added to the blood specimen) up to completion of the coagulation. Based on the optical information or physical information that has been continuously or intermittently measured in a series of process from the start of the measurement to the completion of the coagulation, a parameter concerning differentiation of a coagulation waveform as described below can be obtained at any point of time or in any time in the process. Furthermore, the total reaction time described below can be obtained from such a coagulation waveform.

The measurement time may be determined as appropriate according to a blood specimen. In the present embodiment, the measurement time can be determined to be, for example, not shorter than 4 seconds and not longer than 500 seconds. In the method according to the present embodiment, when normal plasma (plasma collected from a healthy person) is used as a blood specimen, coagulation is completed within 15 seconds from preparation of the measurement sample in general.

In the preferred embodiment, a coagulation waveform is obtained from optical information obtained by light being applied to the measurement sample. Examples of the optical information include an amount of scattered light, a transmitted light intensity, and an absorbance that are continuously or intermittently measured. In this case, the coagulation waveform is a waveform that represents temporal change of an amount of scattered light, a transmitted light intensity, or an absorbance. Light applied to a measurement sample may be light that is generally used for measuring a coagulation time, and may be, for example, light having a wavelength of approximately 660 nm, and is preferably light having a wavelength of 660 nm. A light source is not particularly limited, and is, for example, a light emitting diode or a halogen lamp.

The coagulation waveform obtained in the present embodiment includes a curve itself of a coagulation waveform and data of the plots of the coagulation waveform. Examples of the data of the plots of the coagulation waveform include a time from a measurement start point and a measured value of optical characteristics or physical characteristics of the measurement sample at a point of the time.

With reference to FIG. 1, a typical coagulation waveform representing temporal change of a transmitted light intensity will be described. In FIG. 1, a point A represents a point of time when a blood specimen and a thrombin-containing reagent are mixed, and also represents a point of time when measurement is started. After that, the coagulation reaction progresses to form fibrin, and change of the transmitted light intensity starts (point B in FIG. 1). As formation of fibrin progresses, the transmitted light intensity is reduced, and, when almost all the fibrinogen has been consumed, the reaction converges, and the transmitted light intensity no longer changes (point C in FIG. 1). The coagulation time may be, for example, a time when the change amount (dH) of the transmitted light intensity is 50% in a case where a change amount (dH), of the transmitted light intensity, which is a difference between the transmitted light intensity (uncoagulated level) at point B when the coagulation reaction starts, and the transmitted light intensity at point C when the transmitted light intensity no longer changes, is 100%. In the preferred embodiment, the coagulation time is a time when the change amount (dH) of the optically measured value is 50% in the coagulation waveform obtained in the optical measurement.

In a case where an automatic blood coagulation measurement device is used, the coagulation time can be calculated by a method such as a percent method, a primary differential method, a secondary differential method, and an inflection point method. When a device that obtains an amount of scattered light as the optical information is used, the percent method is a method in which, when a certain proportion of change of an amount of scattered light from the start of the reaction to the end thereof is used as a threshold value, a time at which the threshold value is exceeded is set as a coagulation time. For example, when the threshold value is 50% of change of an amount of scattered light, a coagulation time t is calculated by solving an equation in which $E_{range}^{(1)-2} \times 0.5 + E_b$=right side of expression (A) is satisfied. The expression (A) is indicated below.

[Formula 1]

$$E(t) = \frac{E_{range}}{\left\{1 + \exp\left(\frac{t-a}{k}\right)\right\}^b} + E_b \quad (A)$$

In expression (A), $E_{range}$ represents a difference between a maximum value $E_p$ and a minimum value $E_b$ of a scattered light intensity E, a represents a time t at an inflection point of an approximate curve of a coagulation waveform, k represents a slope of a curve in a region between a base line region and a plateau region of the approximate curve, and b represents a correction parameter. The primary differential method is a method in which a time when a differential value (change of an amount of scattered light) of an amount of scattered light is maximum is used as the coagulation time. The primary differentiation of an approximate expression obtained by substituting $E_{range}^{(1)-2}$, $a^{(1)-2}$, $b^{(1)-2}$, $k^{(1)-2}$, and $E_b^{(1)-2}$ into expression (A) is performed to calculate the maximum value. The secondary differential method is a method in which a time when the secondary differential value of an amount of scattered light is maximum is used as the coagulation time. The secondary differentiation of an approximate expression obtained by substituting $E_{range}^{(1)-2}$, $a^{(1)-2}$, $b^{(1)-2}$, $k^{(1)-2}$, and $E_b^{(1)-2}$ into expression (A) is performed to calculate the maximum value. The inflection point method is a method in which $a^{(1)-2}$ is used as the coagulation time as it is. For these coagulation time calculation methods, WO2014/162878 can be referred to.

Figure 2:
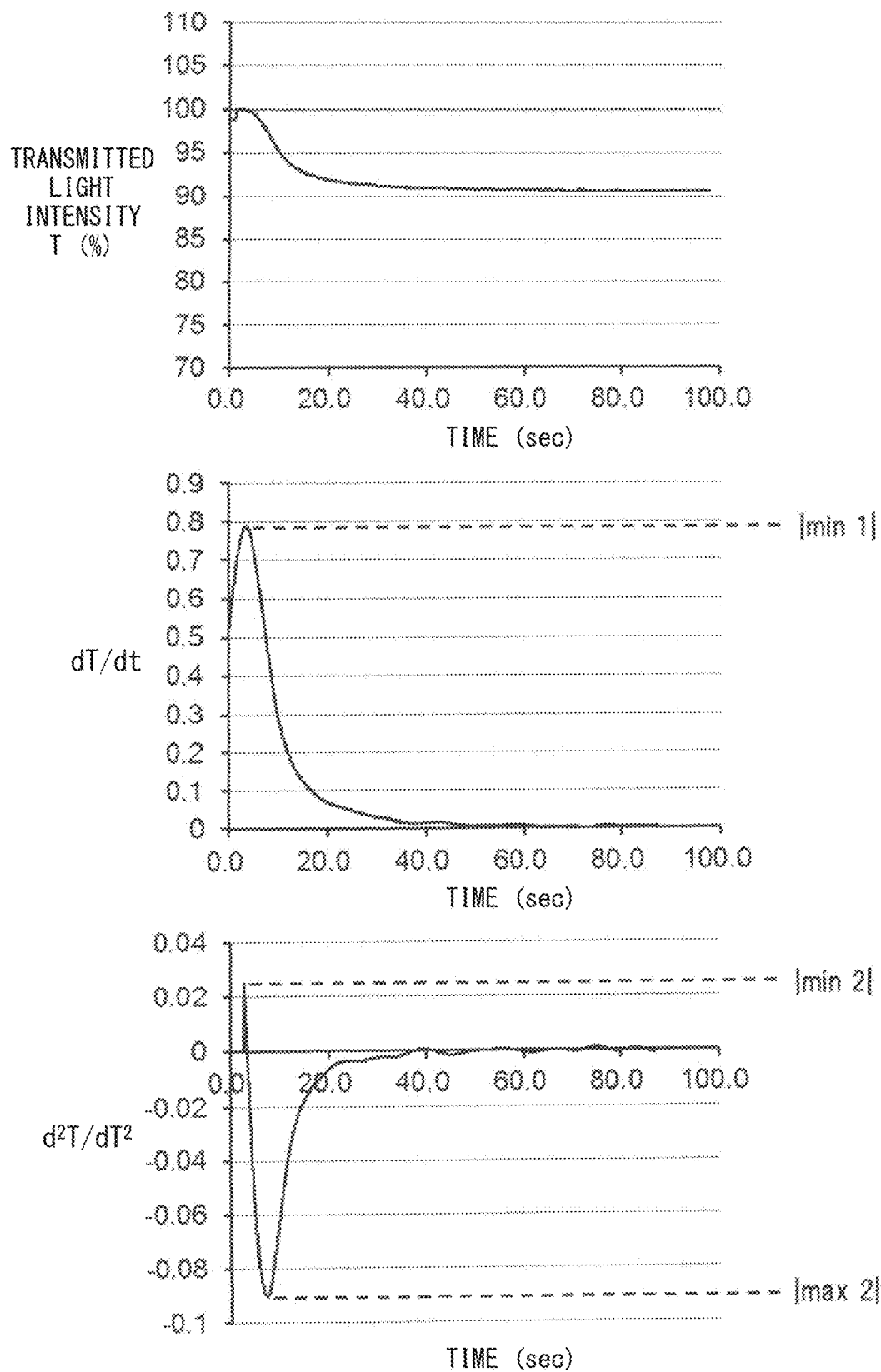
FIG. 2 shows examples of graphs of a coagulation waveform of normal plasma, a primary differentiation thereof, and a secondary differentiation thereof.

In the method for analyzing a blood specimen according to the first mode, a value of a parameter (hereinafter, also referred to as "differentiation parameter") concerning differentiation of a coagulation waveform is obtained based on the coagulation waveform. The differentiation parameter may be a parameter that is obtained from a waveform of a coagulation speed which is obtained by differentiating a coagulation waveform, or from waveforms of an acceleration and a deceleration of coagulation which are obtained by differentiating a waveform of the coagulation speed. With reference to FIG. 2, a waveform of a speed and waveforms of an acceleration and a deceleration will be described. By differentiation (primary differentiation) of a coagulation waveform (graph in the upper portion in FIG. 2), a waveform (graph in the mid-portion in FIG. 2) representing change of a coagulation speed is obtained. By differentiation (secondary differentiation) of the waveform of the speed, a waveform (graph in the lower portion in FIG. 2) representing change of an acceleration and a deceleration of coagulation is obtained. In FIG. 2, the waveform is represented such that the coagulation speed (dT/dt) has a positive value. However, the waveform may be represented such that the coagulation speed has a negative value. That is, waveforms in the graphs in the mid-portion and the lower portion in FIG. 2 may be obtained by inverting the positive and the negative values in the vertical axis.

Examples of the differentiation parameter include, but are not limited to, |min 1|, |max 2|, |min 2|, an area under a curve (AUC), and a time (|min 1| time) until the coagulation speed becomes maximal. A typical differentiation parameter will be described. |min 1| represents an absolute value of a peak value in a waveform of speed, and represents the maximum coagulation speed. |min 2| represents an absolute value of a peak value of a coagulation acceleration, and represents the maximum coagulation acceleration. |max 2| represents an absolute value of a peak value of a coagulation deceleration, and represents the maximum coagulation deceleration. The terms themselves of |min 1|, |min 2|, and |max 2| are known in this field of technique. "AUC" represents a value of an area of a region surrounded by a curve of the waveform, the horizontal axis (axis representing time), and the vertical axis (axis representing speed) in the waveform of speed. |min 1| time represents a time from the measurement start time to a time when the coagulation speed indicates the maximum value (value of |min 1|) in the waveform of speed. Among them, |min 1| and |max 2| are preferable. The differentiation parameter may be calculated from the coagulation waveform in a hand method. In a case where an automatic blood coagulation measurement device is used to obtain the coagulation waveform, the differentiation parameter can be obtained by the device.

In the method for analyzing a blood specimen according to the seventh mode, the total reaction time is obtained based on a coagulation waveform. The total reaction time represents a time, in the coagulation waveform, from a time when a blood specimen and a thrombin-containing reagent are mixed, up to a time when a measured value of the coagulation waveform no longer changes. A point of time (hereinafter, simply referred to as "end point") when the measured value of the coagulation waveform no longer changes represents a point of time when change of a measured value of optical characteristics or physical characteristics of the measurement sample is no longer seen in the coagulation waveform. For example, in the coagulation waveform shown in FIG. 1, the end point is point C, and the total reaction time is a time from A to C. The total reaction time may be calculated from the coagulation waveform in a hand method. In a case where an automatic blood coagulation measurement device is used for measurement, the total reaction time can be obtained by the device.

When a coagulation waveform representing temporal change of a transmitted light intensity is obtained, the end point may be determined by, for example, any one of the following methods 1 to 3. These methods are adopted in CS-5100 of the automatic blood coagulation measurement device (SYSMEX CORPORATION).

Figure 3A:
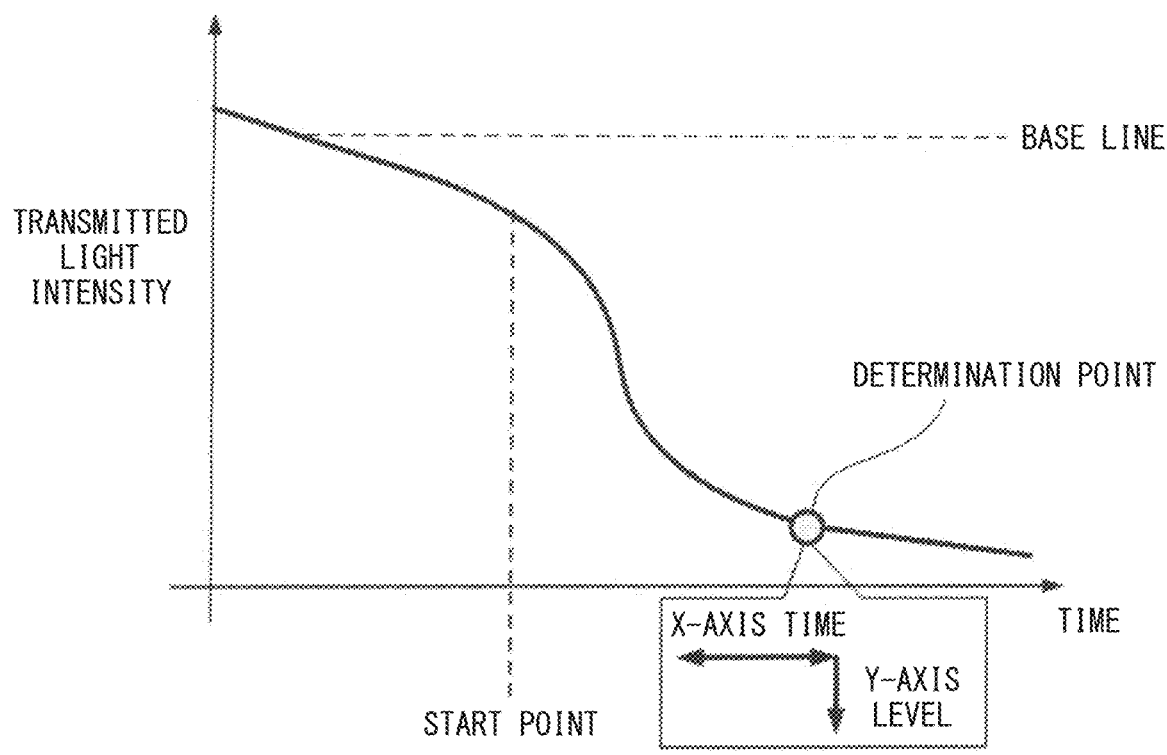
FIG. 3A illustrates method 1 for determining a point of time, in a coagulation waveform, when coagulation reaction has ended.

Method 1: When change of a transmitted light intensity in a section from a determination point to a time which is behind the determination point by an X-axis time at and after a point of time (hereinafter, also referred to as "start point") when the coagulation reaction starts is within the Y-axis level, the determination point is set as the end point (see FIG. 3A). The X-axis time and the Y-axis level can be set as appropriate. The coagulation start point may be a point of time when the transmitted light intensity from the base line becomes higher than or equal to a predetermined value. The base line may represent a transmitted light intensity at a time when the transmitted light intensity becomes maximal within a predetermined time (for example, 60 seconds) from start of the measurement.

Figure 3B:
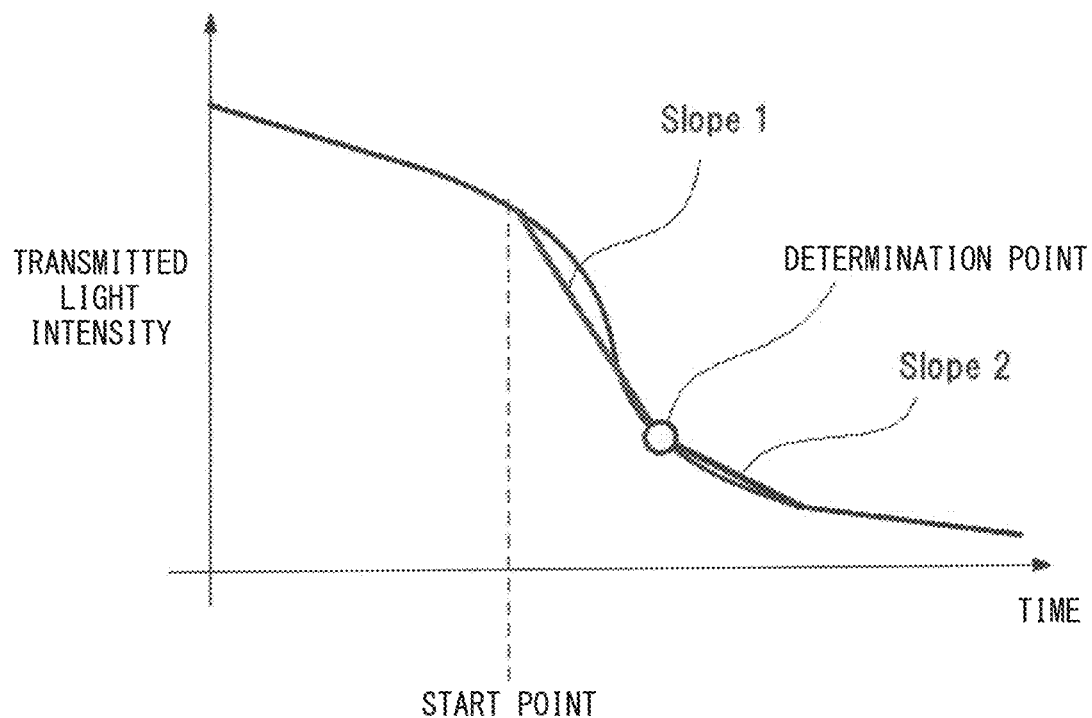
FIG. 3B illustrates method 2 for determining a point of time, in a coagulation waveform, when coagulation reaction has ended.

Method 2: A slope (Slope1) in a section from the start point to the determination point, and a slope (Slope2) at and after the determination point (the same width as that in the section from the start point to the determination point) are calculated (see FIG. 3B). When a ratio (Slope2/Slope1) between the slopes is less than a predetermined value, the determination point is set as the end point. The predetermined value can be set as appropriate.

Figure 3C:
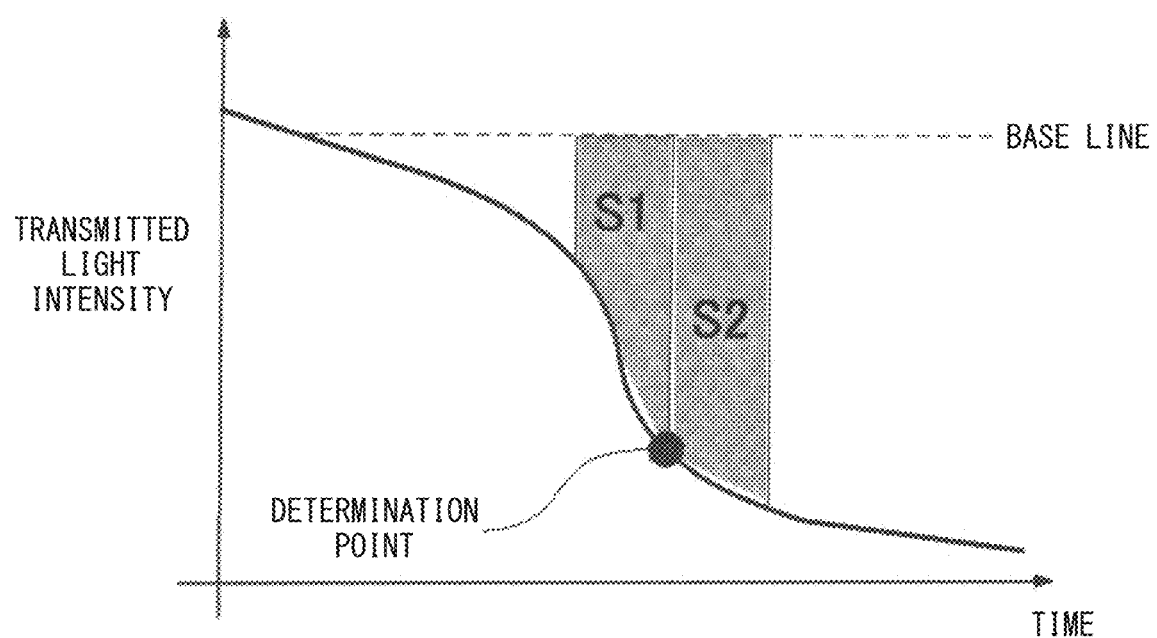
FIG. 3C illustrates method 3 for determining a point of time, in a coagulation waveform, when the coagulation reaction has ended.

Method 3: The determination point is set as a base point, and areas (S1 and S2) before and after the determination point over any section width are calculated (see FIG. 3C). In FIG. 3C, an area of a region surrounded by the base line having the section width and a curve of the coagulation waveform is calculated. When a ratio (S2/S1) between the areas before and after the determination point is less than a predetermined value, the determination point is set as the end point. The predetermined value can be set as appropriate.

In the method for analyzing a blood specimen according to the first mode, the number of the differentiation parameters to be obtained may be one, or may be greater than or equal to two. Furthermore, the differentiation parameter may be a value obtained by two or more differentiation parameters being combined. For example, the sum of at least two values selected from |min 1|, |max 2|, |min 2|, the AUC, and the |min 1| time, the difference therebetween, the product thereof, or the ratio therebetween may be used.

In the present embodiment, information concerning an amount of antigen of fibrinogen is obtained based on at least one of values of parameters concerning differentiation of the obtained coagulation waveform, or based on the total reaction time. An amount of antigen of fibrinogen represents an amount of protein, in fibrinogen, obtained by immunological measurement using an anti-fibrinogen antibody. The information concerning an amount of antigen of fibrinogen may be information that quantitatively or semi-quantitatively indicates an amount of antigen of fibrinogen. The information that quantitatively indicates an amount of antigen of fibrinogen may be, for example, an estimated value or conversion value, of an amount of antigen of fibrinogen, which is calculated from a value of the differentiation parameter or the total reaction time.

The information that semi-quantitatively indicates an amount of antigen of fibrinogen may be, for example, information that indicates an amount of antigen of fibrinogen stepwise as "little", "a little" "normal", "much", or the like. Furthermore, the stepwise information such as "little", "a little", "normal", and "much" may be indicated as numerals representing levels such as 1, 2, 3, and 4. The information that semi-quantitatively indicates an amount of antigen of fibrinogen may be obtained based on the information that quantitatively indicates an amount of antigen of fibrinogen.

The information concerning an amount of antigen of fibrinogen is preferably an estimated value or conversion value, of an amount of antigen of fibrinogen, which is calculated from a value of the differentiation parameter or the total reaction time. In the present embodiment, preferably, a value of a differentiation parameter or the total reaction time, and an amount of antigen of fibrinogen by an immunological measurement are obtained in advance for each of a plurality of normal specimens, and these values are plotted into graphs to generate calibration curves. Furthermore, a regression equation for the obtained calibration curve may be generated. The value of the differentiation parameter or the total reaction time can be converted to a value of an amount of antigen of fibrinogen according to the obtained calibration curve or regression equation. Examples of the normal specimen include blood specimens collected from healthy persons or commercially available normal plasma.

In the present embodiment, information concerning an amount of antigen of fibrinogen may be obtained by using not only a value of a differentiation parameter itself or a value of the total reaction time itself, but also values calculated from them. Examples of a value calculated from a value of a differentiation parameter include a value obtained by multiplying the value of the parameter by a constant, a value obtained by adding a constant to the value of the parameter, a value obtained by subtracting a constant from the value of the parameter, a reciprocal of the value of the parameter, and a value obtained by combination of these calculations. The value calculated from the total reaction time can be also obtained in the same manner as described above.

In the present embodiment, a value of an amount of antigen of fibrinogen is preferably obtained from a value of |min 1| or |max 2| among values of the differentiation parameter. A value of an amount of antigen of fibrinogen is particularly preferably obtained from a value of |min 1|. In this case, a value of an amount of antigen of fibrinogen is more preferably obtained by converting a value of |min 1| or |max 2| to the value of the amount of antigen of fibrinogen by using a calibration curve or regression equation. In the method for analyzing a blood specimen according to the seventh mode, a value of an amount of antigen of fibrinogen is more preferably obtained by converting a value of the total reaction time to the value of the amount of antigen of fibrinogen by using a calibration curve or regression equation.

In the present embodiment, a coagulation time may be further obtained based on the coagulation waveform. Furthermore, information concerning an active concentration of fibrinogen as described below may be obtained based on the obtained coagulation time. Thus, not only information concerning an amount of antigen of fibrinogen but also information concerning an active concentration of fibrinogen or a coagulation time associated with coagulability of fibrinogen can be obtained from a result of measurement of the coagulation waveform.

[2. Method for Analyzing Blood Specimen for Obtaining Information Concerning Function of Fibrinogen]

In the method for analyzing a blood specimen according to each of the first and the seventh modes, information concerning an amount of antigen of fibrinogen is obtained by measuring a coagulation waveform according to a thrombin time method for measuring activity of fibrinogen as described above. In a method for analyzing a blood specimen according to each of a second and an eighth modes, information concerning function of fibrinogen can be obtained by obtaining a coagulation time in addition to the differentiation parameter or the total reaction time.

In the present embodiment, the function of fibrinogen represents coagulability, of fibrinogen, initiated by addition of thrombin. The information concerning the function of fibrinogen may be quantitative information of the function of fibrinogen or qualitative information of the function. As the quantitative information of the function of fibrinogen, information concerning a ratio between an amount of antigen of fibrinogen, and the activity is preferable. As the qualitative information of the function of fibrinogen, information indicating whether or not abnormality in fibrinogen occurs is preferable.

In the present embodiment, firstly, a blood specimen and a thrombin-containing reagent are mixed, to coagulate the blood specimen, and a coagulation waveform is obtained. Details of the blood specimen, the thrombin-containing reagent, and the coagulation waveform, and obtaining of the coagulation waveform are the same as described for the first mode and the seventh mode.

In the method for analyzing a blood specimen according to the second mode, at least one of values of parameters concerning differentiation of the coagulation waveform, and a coagulation time are obtained based on the coagulation waveform. In the method for analyzing a blood specimen according to the eighth mode, the total reaction time and the coagulation time are obtained based on the coagulation waveform. Details and obtaining of values of parameters concerning differentiation of the coagulation waveform and the total reaction time, are the same as described for the first mode and the seventh mode.

In the present embodiment, the coagulation time is preferably a time when an amount of change of an optically measured value is 50% in a case where an amount of change (dH), of the optically measured value, which represents a difference between an optically measured value at the start of the coagulation reaction and an optically measured value at a time when the optically measured value no longer changes, is 100% in the coagulation waveform (see FIG. 1). As the optically measured value, a transmitted light intensity is preferable. In a case where the coagulation time is measured in a hand method, the coagulation time may be obtained as a time from a point of time when a blood specimen and a thrombin-containing reagent are mixed, to a point of time when fibrin is deposited and coagulated in the measurement sample. The measurement itself of the coagulation time in the hand method is known in this field of technique.

(Obtaining Information Concerning Ratio Between Amount of Antigen of Fibrinogen, and Activity)

An embodiment in which information concerning a ratio between an amount of antigen of fibrinogen and the activity is obtained as information concerning a function of fibrinogen will be described below. In the present embodiment, information concerning an amount of antigen of fibrinogen is obtained based on at least one of values of parameters concerning differentiation of a coagulation waveform, or the total reaction time, and information concerning an active concentration of fibrinogen is obtained based on a coagulation time. Details and obtaining of the information concerning an amount of antigen of fibrinogen are the same as described for the first mode and the seventh mode. In the present embodiment, the information concerning an amount of antigen of fibrinogen is preferably a value of an amount of antigen of fibrinogen.

The active concentration of fibrinogen represents a concentration, of fibrinogen in a blood specimen, obtained from a coagulation time according to the thrombin time method in a case where the coagulability of fibrinogen in the blood specimen is assumed to be normal. The information concerning the active concentration of fibrinogen may be information that quantitatively or semi-quantitatively indicates the active concentration of fibrinogen. The information that quantitatively indicates the active concentration of fibrinogen may be, for example, a value of the active concentration of fibrinogen. A method itself for obtaining the active concentration of fibrinogen is known in this field of technique. For example, a coagulation time of a blood specimen can be assigned to a conversion table or a calibration curve that is generated according to a coagulation time of fibrinogen standard solution the concentration of which is known, to obtain the active concentration of fibrinogen.

The information that semi-quantitatively indicates the active concentration of fibrinogen may be, for example, information that indicates the active concentration of fibrinogen stepwise as "almost none", "low", "normal", "high", or the like. Furthermore, the stepwise information such as "almost none", "low", "normal", and "high" may be indicated as numerals representing levels such as 1, 2, 3, and 4. The information that semi-quantitatively indicates the active concentration of fibrinogen may be obtained based on the information that quantitatively indicates the active concentration of fibrinogen.

In the present embodiment, the information concerning the active concentration of fibrinogen is preferably a value of the active concentration of fibrinogen.

In the present embodiment, information concerning a ratio between an amount of antigen of fibrinogen, and the activity is obtained based on information concerning an amount of antigen of fibrinogen and information concerning an active concentration of fibrinogen. The information concerning the ratio may be information or a numerical value that represents comparison between an amount of antigen and the activity. When the information concerning an amount of antigen of fibrinogen and the information concerning an active concentration of fibrinogen are semi-quantitative information, information that represents comparison between the amount of antigen and the active concentration may be, for example, information such as "the amount of antigen: the active concentration=(normal): (low)" or "the amount of antigen: the active concentration=3:1". The numerical value that represents comparison between the amount of antigen and the active concentration is, for example, a value of a ratio between a value of the active concentration of fibrinogen and a value of the amount of antigen of fibrinogen.

In the present embodiment, the information concerning a ratio between an amount of antigen of fibrinogen, and the activity, is preferably a value of a ratio between a value of an active concentration of fibrinogen and a value of an amount of antigen of fibrinogen. The value of the ratio can be calculated according to the following expression (1) or (2).

(Value of ratio)=(value of active concentration of fibrinogen)/(value of amount of antigen of fibrinogen)     expression (1) or (Value of ratio)=(value of amount of antigen of fibrinogen/(value of active concentration of fibrinogen)     expression (2)

The value of the ratio calculated by expression (1) represents an activity value of fibrinogen per a predetermined amount of antigen, and corresponds to a specific activity of fibrinogen. The value of the ratio calculated by expression (2) corresponds to a reciprocal of the specific activity of fibrinogen. Thus, a value representing the specific activity of fibrinogen can be obtained by measurement of the coagulation waveform according to the thrombin time method.

(Obtaining Information Concerning Abnormality in Fibrinogen)

An embodiment in which information indicating whether or not abnormality in fibrinogen occurs is obtained as information concerning the function of fibrinogen will be described below. In the present embodiment, whether or not abnormality in fibrinogen occurs can be determined, by obtaining information concerning an amount of antigen of fibrinogen and information concerning an active concentration of fibrinogen, from a result of measurement of the coagulation waveform according to the thrombin time method.

In the present embodiment, firstly, a blood specimen and a thrombin-containing reagent are mixed to coagulate the blood specimen, and a coagulation waveform is obtained. Details of the blood specimen, the thrombin-containing reagent, and the coagulation waveform, and obtaining of the coagulation waveform are the same as described for the first mode and the seventh mode.

Next, in the method for analyzing a blood specimen according to the second mode, at least one of values of parameters concerning differentiation of a coagulation waveform, and a coagulation time are obtained based on the coagulation waveform. In the method for analyzing a blood specimen according to the eighth mode, a total reaction time and a coagulation time are obtained based on a coagulation waveform. Details and obtaining of the value of the parameter concerning differentiation of the coagulation waveform, the total reaction time, and the coagulation time are as described above.

The information concerning an amount of antigen of fibrinogen is obtained based on at least one of values of parameters concerning differentiation of the coagulation waveform, or the total reaction time, and the information concerning an active concentration of fibrinogen is obtained based on the coagulation time. Details and obtaining of the information concerning an amount of antigen of fibrinogen and the information concerning the active concentration of fibrinogen are as described above.

In the present embodiment, information indicating whether or not abnormality in fibrinogen occurs is obtained based on the information concerning an amount of antigen of fibrinogen and the information concerning an active concentration of fibrinogen. Abnormality in fibrinogen may be abnormality (quantitative abnormality) of an amount of antigen of fibrinogen or abnormality (qualitative abnormality) of activity of fibrinogen.

In the present embodiment, for example, in a case where information or a numerical value indicating that an amount of antigen of fibrinogen is little or a little is obtained, and information or a numerical value indicating that the active concentration of fibrinogen is low or almost none, is obtained, it may be determined that an amount of antigen of fibrinogen is abnormal. In a case where information or a numerical value indicating that an amount of antigen of fibrinogen is normal is obtained, and information or a numerical value indicating that the active concentration of fibrinogen is low or almost none, is obtained, it may be determined that activity of fibrinogen is abnormal. Thus, information indicating whether or not abnormality in fibrinogen occurs can be obtained.

The above-described determination is preferably performed by comparison with information concerning an amount of antigen of fibrinogen and information concerning an active concentration of fibrinogen in a normal specimen. For example, in a case where a value of an amount of antigen of fibrinogen in a blood specimen is less than a value of the amount of antigen of fibrinogen in the normal specimen, information indicating that the amount of antigen of fibrinogen in the blood specimen is little or a little, can be obtained. In a case where a value of an active concentration of fibrinogen in the blood specimen is less than a value of the active concentration of fibrinogen in the normal specimen, the information indicating that the active concentration of fibrinogen in the blood specimen is low or almost none, can be obtained.

In the present embodiment, the information concerning an amount of antigen of fibrinogen is preferably a value of an amount of antigen of fibrinogen. The information concerning an active concentration of fibrinogen is preferably a value of an active concentration of fibrinogen.

In a case where whether or not the activity of fibrinogen is abnormal is determined, information concerning a ratio between an amount of antigen of fibrinogen, and the activity is obtained based on the information concerning the amount of antigen of fibrinogen and the information concerning the active concentration of fibrinogen, and the determination may be performed based on the information concerning the ratio. Details and obtaining of the information concerning a ratio between an amount of antigen and the activity are as described above. In the present embodiment, the information concerning a ratio between an amount of antigen of fibrinogen and the activity is preferably a value of a ratio between a value of an active concentration of fibrinogen and a value of an amount of antigen of fibrinogen. The value of the ratio can be calculated according to expression (1) or (2) described above.

As described above, the value of the ratio calculated by expression (1) corresponds to the specific activity of fibrinogen, and the value of the ratio calculated by expression (2) corresponds to a reciprocal of the specific activity of fibrinogen. Therefore, by these values being each compared with a predetermined threshold value, abnormality of activity of fibrinogen can be easily determined. For example, in a case where the value of the ratio calculated by expression (1) is compared with a first threshold value, when the value of the ratio calculated by expression (1) is less than the first threshold value, it can be determined that the activity of fibrinogen is abnormal. Meanwhile, in a case where the value of the ratio calculated by expression (1) is greater than the first threshold value or equal to the first threshold value, it may be determined that the activity of fibrinogen is not abnormal.

Alternatively, in a case where the value of the ratio calculated by expression (2) is compared with a second threshold value, when the value of the ratio calculated by expression (2) is greater than the second threshold value, it can be determined that the activity of fibrinogen is abnormal. Meanwhile, in a case where the value of the ratio calculated by expression (2) is less than the second threshold value or equal to the second threshold value, it may be determined that the activity of fibrinogen is not abnormal.

In the present embodiment, the first and the second threshold values are not particularly limited. For example, the first and the second threshold values may be empirically set by accumulating coagulation waveform parameters and data of coagulation times for blood specimens of healthy persons. Alternatively, the values of the ratios calculated by expressions (1) and (2) from the values of amounts of antigen of fibrinogen and the values of the active concentrations, which are measured for a plurality of normal specimens, may be set as the first and the second threshold values.

[3. Blood Specimen Analyzer and Computer Program]

An example of a blood specimen analyzer according to the present embodiment will be described below with reference to the drawings. However, the present embodiment is not limited only to this example. Hereinafter, the blood specimen analyzer will be simply referred to also as "analyzer".

Figure 4:
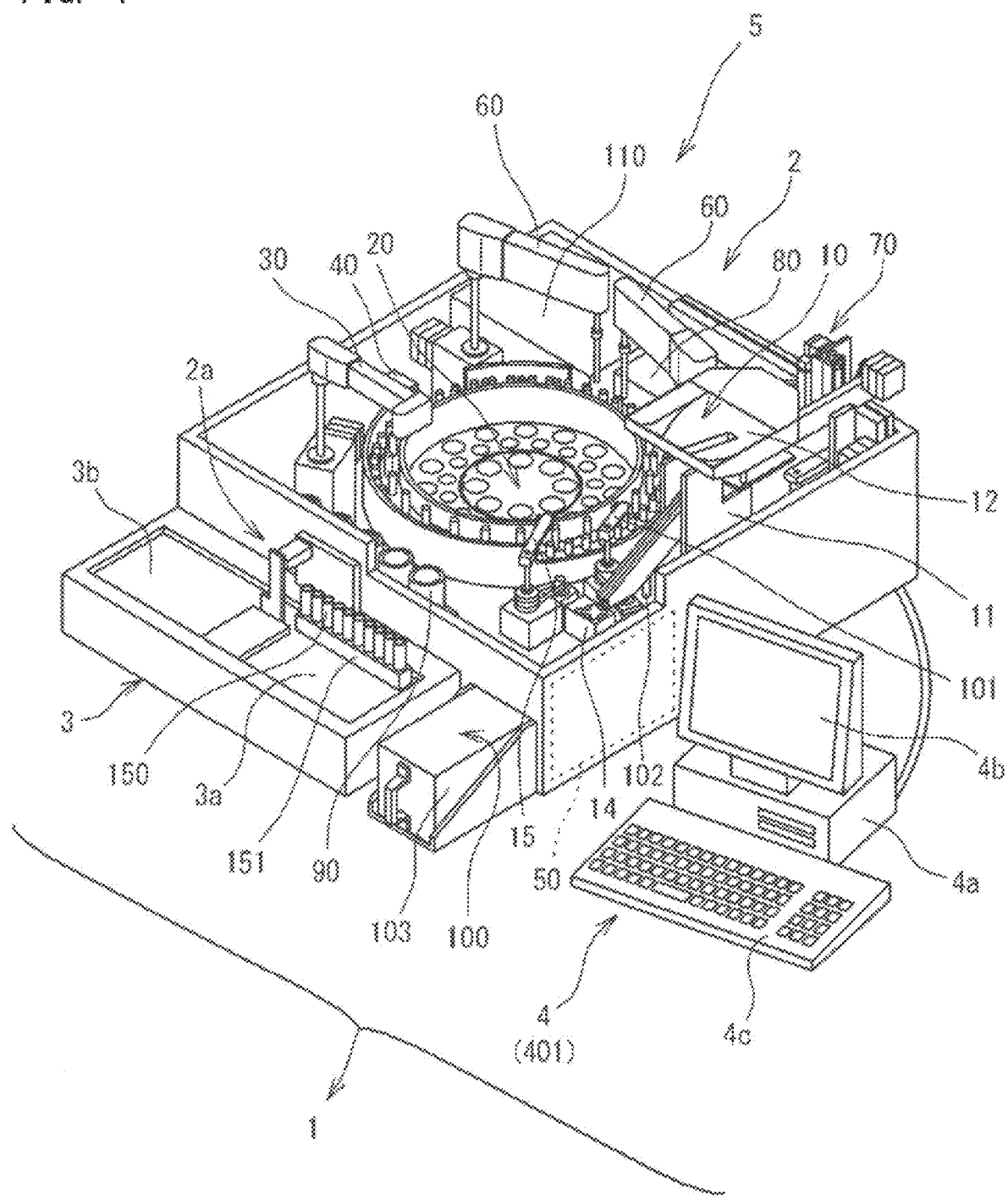
FIG. 4 is a perspective view of the entirety of a structure of a blood specimen analyzer.

As shown in FIG. 4, the analyzer 1 includes a measurement device 5 that prepares and measures a measurement sample, and a control device 4 that analyzes measurement data obtained by the measurement device 5 and provides the measurement device 5 with instructions. The measurement device 5 includes a measurement unit 2 that obtains optical information or physical information from the measurement sample, and a specimen transport unit 3 disposed in front of the measurement unit 2. In the present embodiment, the specimen transport unit 3 and the measurement unit 2 are integrated to form a part of the analyzer 1. In another embodiment, the specimen transport unit 3 may be provided separately from the analyzer 1. For example, in a large scale of system that includes a plurality of analyzers, the plurality of analyzers may be connected to a large transport line without providing the specimen transport unit in each analyzer.

(Structure of Measurement Device)

The measurement unit 2 of the measurement device 5 is capable of obtaining, by optically measuring a specimen supplied from the specimen transport unit 3, optical information concerning the supplied specimen. In the present embodiment, the blood specimen, which is dispensed from a test tube 150 placed in a rack 151 of the specimen transport unit 3 into cuvettes 152 (see FIG. 5) in the measurement unit 2, is optically measured.

Figure 5:
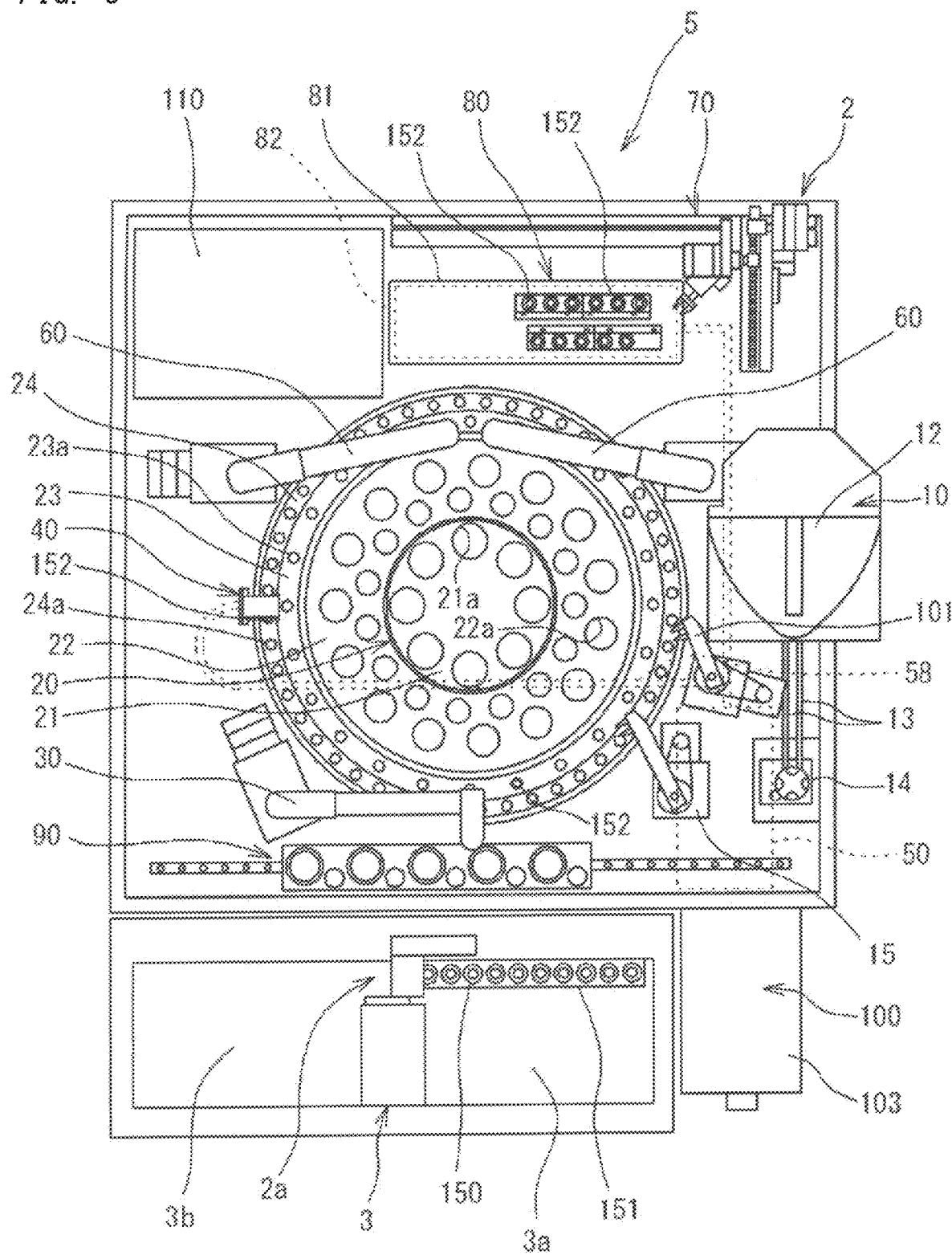
FIG. 5 is a plan view of an inside of a measurement device of the blood specimen analyzer as viewed from thereabove.
Figure 6:
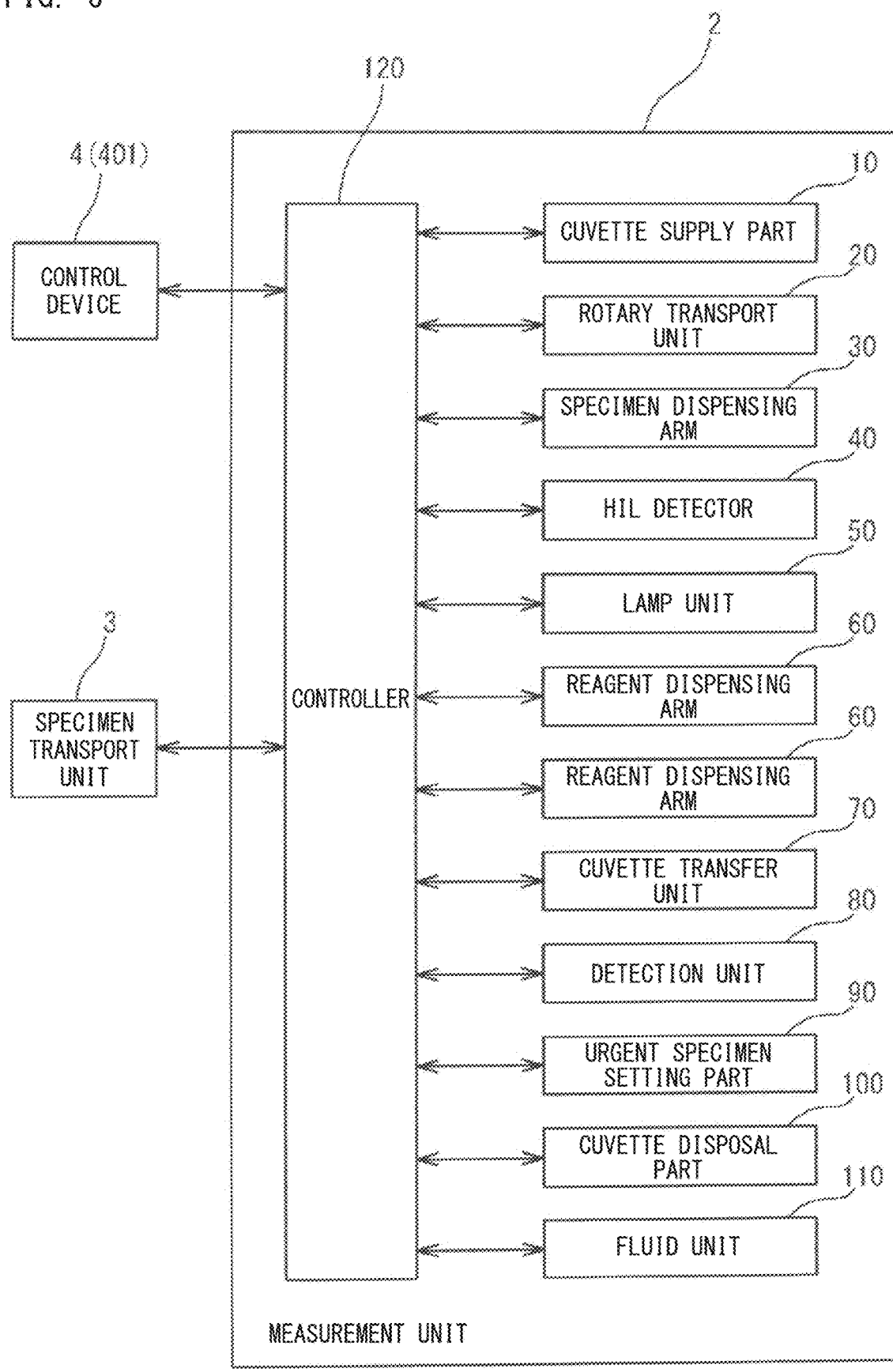
FIG. 6 illustrates a configuration of the measurement device of the blood specimen analyzer.

As shown in FIG. 4 and FIG. 5, the measurement unit 2 includes a cuvette supply part 10, a rotary transport unit 20, a specimen dispensing arm 30, an HIL detector 40, a lamp unit 50, two reagent dispensing arms 60, a cuvette transfer unit 70, a detection unit 80, an urgent specimen setting part 90, a cuvette disposal part 100, a fluid unit 110, and a controller 120 (see FIG. 6). In the present embodiment, the measurement unit 2 functions as a measurement sample preparation unit that prepares a measurement sample from a blood specimen, and as a measurement unit that measures the prepared measurement sample. The controller 120 functions to control operations of mechanisms in the measurement unit 2 and the specimen transport unit 3.

In the present embodiment, the measurement sample preparation unit includes the cuvette supply part 10, the rotary transport unit 20, the specimen dispensing arm 30, and the two reagent dispensing arms 60. The measurement sample preparation unit may further include a reagent table 21, a reagent table 22, a secondary dispensing table 23, and a primary dispensing table 24, which will be described below.

The cuvette supply part 10 is structured so as to be capable of sequentially supplying a plurality of the cuvettes 152 inserted by a user, to the rotary transport unit 20. The cuvette supply part 10 includes a hopper 12 mounted to an apparatus body through a bracket 11 (see FIG. 4), two guiding plates 13 provided below the hopper 12, a support base 14 disposed at the lower ends of the two guiding plates 13, and a supply catcher part 15 disposed so as to be spaced from the support base 14 over a predetermined distance, as shown in FIG. 5. The two guiding plates 13 are disposed in parallel with each other so as to be spaced from each other over a distance that is less than the diameter of a flange portion of the cuvette 152, and greater than the diameter of a trunk portion of the cuvette 152. The cuvette 152 supplied in the hopper 12 slides and moves toward the support base 14 in a state where the flange portion contacts with the upper surfaces of the two guiding plates 13. The support base 14 functions to rotate and transfer the cuvette 152 that has slid and moved on the guiding plates 13, to a position at which the supply catcher part 15 can hold the cuvette 152. The supply catcher part 15 is provided so as to supply, to the rotary transport unit 20, the cuvette 152 having been rotated and transferred by the support base 14.

The rotary transport unit 20 is provided so as to transport, in the rotating direction, the cuvette 152 supplied from the cuvette supply part 10, and a reagent container (not shown) that contains a reagent to be added to the blood specimen in the cuvette 152. The rotary transport unit 20 includes the round reagent table 21, the annular reagent table 22 disposed outside the round reagent table 21, the annular secondary dispensing table 23 disposed outside the annular reagent table 22, and the annular primary dispensing table 24 disposed outside the annular secondary dispensing table 23, as shown in FIG. 5. Each of the primary dispensing table 24, the secondary dispensing table 23, the reagent table 21, and the reagent table 22 is structured so as to be rotatable independently in both the clockwise direction and the counterclockwise direction.

The reagent table 21 includes a plurality of holes 21a spaced from each other over a predetermined distance along the circumferential direction, and the reagent table 22 includes a plurality of holes 22a spaced from each other over a predetermined distance along the circumferential direction, as shown in FIG. 5. The holes 21a and 22a of the reagent tables 21 and 22 are formed so as to place a plurality of reagent containers (not shown) that contain various reagents to be added when a measurement sample is prepared from a blood specimen. The primary dispensing table 24 includes a plurality of cylindrical holding portions 24a spaced from each other over a predetermined distance along the circumferential direction, and the secondary dispensing table 23 includes a plurality of cylindrical holding portions 23a spaced from each other over a predetermined distance along the circumferential direction. The holding portions 24a and 23a are formed so as to hold the cuvette 152 supplied from the cuvette supply part 10. A specimen contained in the test tube 150 in the specimen transport unit 3 is dispensed into the cuvettes 152 held by the holding portions 24a of the primary dispensing table 24 when primary dispensing is performed. A specimen contained in the cuvette 152 held by the primary dispensing table 24 is dispensed into the cuvettes 152 held by the holding portions 23a of the secondary dispensing table 23 when the secondary dispensing is performed. The holding portion 24a has a pair of small holes at positions that are lateral to the holding portion 24a and oppose each other. The pair of small holes are formed so as to allow passing of light emitted from a bifurcated optical fiber 58 of the lamp unit 50 described below.

The specimen dispensing arm 30 functions to aspirate a specimen contained in the test tube 150 transported to an aspiration position 2a by the specimen transport unit 3, and to dispense the aspirated specimen into the cuvette 152 transferred by the rotary transport unit 20.

The HIL detector 40 is structured so as to obtain optical information from the specimen in order to determine whether or not an interference substance (chyle, hemoglobin, and bilirubin) is included in the blood specimen before a reagent is added, and to measure a concentration of the interference substance. Specifically, whether or not an interference substance is included is determined and a concentration of the interference substance is measured by using four kinds of lights (405 nm, 575 nm, 660 nm, and 800 nm) among five kinds of lights (340 nm, 405 nm, 575 nm, 660 nm, and 800 nm) applied by the lamp unit 50 described below. The light having the wavelength of 405 nm is absorbed by any of chyle, hemoglobin, and bilirubin. That is, the optical information measured by using light having the wavelength of 405 nm includes influence of chyle, hemoglobin, and bilirubin. Light having the wavelength of 575 nm is not substantially absorbed by bilirubin, and is absorbed by chyle and hemoglobin. That is, the optical information measured by using light having the wavelength of 575 nm includes influence of chyle and hemoglobin. Lights having the wavelengths of 660 nm and 800 nm are not substantially absorbed by bilirubin and hemoglobin, and are absorbed by chyle. That is, the optical information measured by using lights having the wavelengths of 660 nm and 800 nm includes influence of chyle. Chyle absorbs light having a wavelength in a band from 405 nm in a short wavelength band to 800 nm in a long wavelength band. Chyle absorbs light having the wavelength of 660 nm more greatly than light having the wavelength of 800 nm. That is, influence of chyle on optical information measured by using light having the wavelength of 800 nm is less than influence of chyle on optical information measured by using light having the wavelength of 660 nm.

The optical information of the specimen is obtained by the HIL detector 40 before optical measurement (main measurement) of the specimen is performed by the detection unit 80. The HIL detector 40 obtains optical information from a specimen in the cuvette 152 held by the holding portion 24a of the primary dispensing table 24 as shown in FIG. 5.

In the present embodiment, the lamp unit 50 is provided so as to supply light used for optical measurement performed by the HIL detector 40 and the detection unit 80, as shown in FIG. 5. That is, one lamp unit 50 is structured so as to be shared by the HIL detector 40 and the detection unit 80.

The reagent dispensing arms 60 are provided so as to mix a reagent into the blood specimen in the cuvette 152 by dispensing, into the cuvette 152 held by the rotary transport unit 20, the reagent in the reagent container (not shown) placed in the rotary transport unit 20, as shown in FIG. 4 and FIG. 5. Thus, the reagent is added to the blood specimen having been optically measured by the HIL detector 40, to prepare a measurement sample. The cuvette transfer unit 70 is provided so as to transfer the cuvette 152 between the rotary transport unit 20 and the detection unit 80. A heating pipette that includes a heating device having a reagent heating function is mounted near the end of the reagent dispensing arms 60.

The detection unit 80 functions to heat the prepared measurement sample, and measure optical information from the measurement sample. The detection unit 80 includes a cuvette setting portion 81, and a detector 82 disposed below the cuvette setting portion 81, as shown in FIG. 5.

Figure 8:
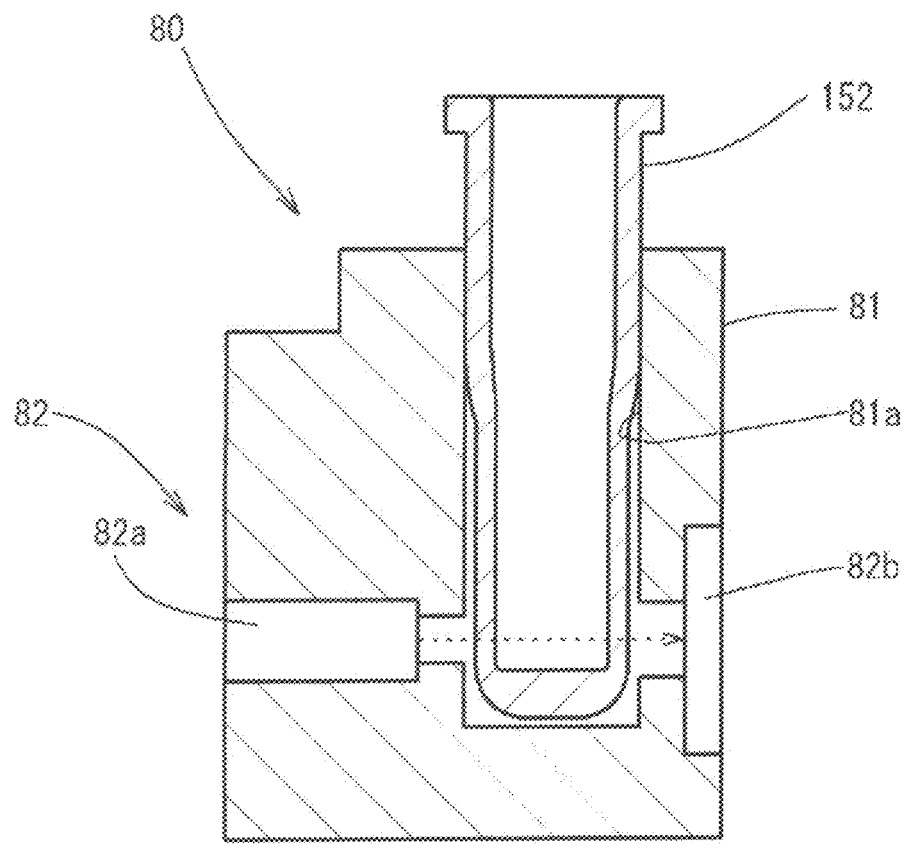
FIG. 8 is a cross-sectional view of a detection unit of the blood specimen analyzer.

With reference to FIG. 8, the cuvette setting portion 81 has a plurality of insertion holes 81a formed therein, and the cuvette 152 is inserted in the insertion hole 81a. The detector 82 includes a light source 82a and a photoelectric conversion element 82b. Light (transmitted light), which is emitted from the light source 82a and is transmitted through the cuvette 152, is received by the photoelectric conversion element 82b. A halogen lump or a LED is used as the light source 82a. A photodiode is used as the photoelectric conversion element 82b. The cuvette setting portion 81 has an insertion hole (not shown) having a heating function.

The urgent specimen setting part 90 is provided so as to analyze a specimen to be urgently analyzed, as shown in FIG. 4 and FIG. 5. The urgent specimen setting part 90 is structured so as to urgently analyze the specimen to be urgently analyzed halfway during analysis of specimens supplied from the specimen transport unit 3. The cuvette disposal part 100 is provided for disposal of the cuvette 152 in the rotary transport unit 20. The cuvette disposal part 100 includes a disposal catcher part 101, a disposal hole 102 (see FIG. 4) spaced from the disposal catcher part 101 over a predetermined distance, and a disposal box 103 disposed below the disposal hole 102, as shown in FIG. 4 and FIG. 5. The disposal catcher part 101 is provided so as to move the cuvette 152 in the rotary transport unit 20 through the disposal hole 102 into the disposal box 103. The fluid unit 110 is provided so as to supply liquid such as washing liquid into a nozzle provided in each dispensing arm when the analyzer 1 is shut down.

With reference to FIG. 6, the cuvette supply part 10, the rotary transport unit 20, the specimen dispensing arm 30, the HIL detector 40, the lamp unit 50, the two reagent dispensing arms 60, the cuvette transfer unit 70, the detection unit 80, the urgent specimen setting part 90, the cuvette disposal part 100, and the fluid unit 110 are connected to the controller 120 so as to be able to communicate an electrical signal thereto and therefrom. The controller 120 includes a CPU, a ROM, a RAM, and the like. The CPU executes a control program which is previously stored in the ROM, to control operations of the mechanisms described above. Thus, the measurement unit 2 performs a measurement operation, a maintenance operation, and the like.

The specimen transport unit 3 of the measurement device 5 functions to transport, to the aspiration position 2a of the measurement unit 2, the rack 151 in which a plurality (10 in the present embodiment) of test tubes 150 that contain the blood specimen are placed, in order to supply the blood specimen to the measurement unit 2, as shown in FIG. 4. The specimen transport unit 3 includes a rack setting region 3a and a rack storage region 3b. In the rack setting region 3a, the rack 151, which stores the test tubes 150 containing specimens having not been treated, are set. In the rack storage region 3b, the rack 151, which stores the test tubes 150 containing specimens having been treated, are stored (Modification of Measurement Unit)

The coagulation waveform may be measured based on physical information representing, for example, change of viscosity due to blood coagulation. In a case where a coagulation waveform is measured based on change of viscosity, the measurement unit 2 includes a high-frequency transmitting coil, a high-frequency receiving coil, a cuvette setting part which is disposed between the high-frequency transmitting coil and the high-frequency receiving coil and in which a cuvette having a steel ball stored therein is disposed, and electromagnets provided at both ends of the cuvette setting part. The steel ball in the cuvette oscillates in the left-right direction due to a magnetic force generated from the electromagnets. The oscillation is reduced as viscosity increases. When coagulation of the measurement sample starts, the viscosity of the measurement sample increases, thereby reducing amplitude of the steel ball. Therefore, the measurement unit 2 detects change of an amplitude by a high-frequency wave transmitted by the high-frequency transmitting coil being received by the high-frequency receiving coil. Furthermore, the control device 4 described below obtains a coagulation waveform based on detected change of amplitude.

(Configuration of Control Device)

As shown in FIG. 4, the control device 4 is implemented by a personal computer 401 (PC) or the like, and includes a controller 4a, a display unit 4b, and a keyboard 4c. The controller 4a functions to control operations of the measurement unit 2 and the specimen transport unit 3, and analyze the optical information, of a specimen, obtained by the measurement unit 2. The controller 4a includes a CPU, a ROM, a RAM, and the like. The display unit 4b displays a result of analysis obtained by the controller 4a, and displays a maintenance history of the analyzer 1 and the like.

Figure 7:
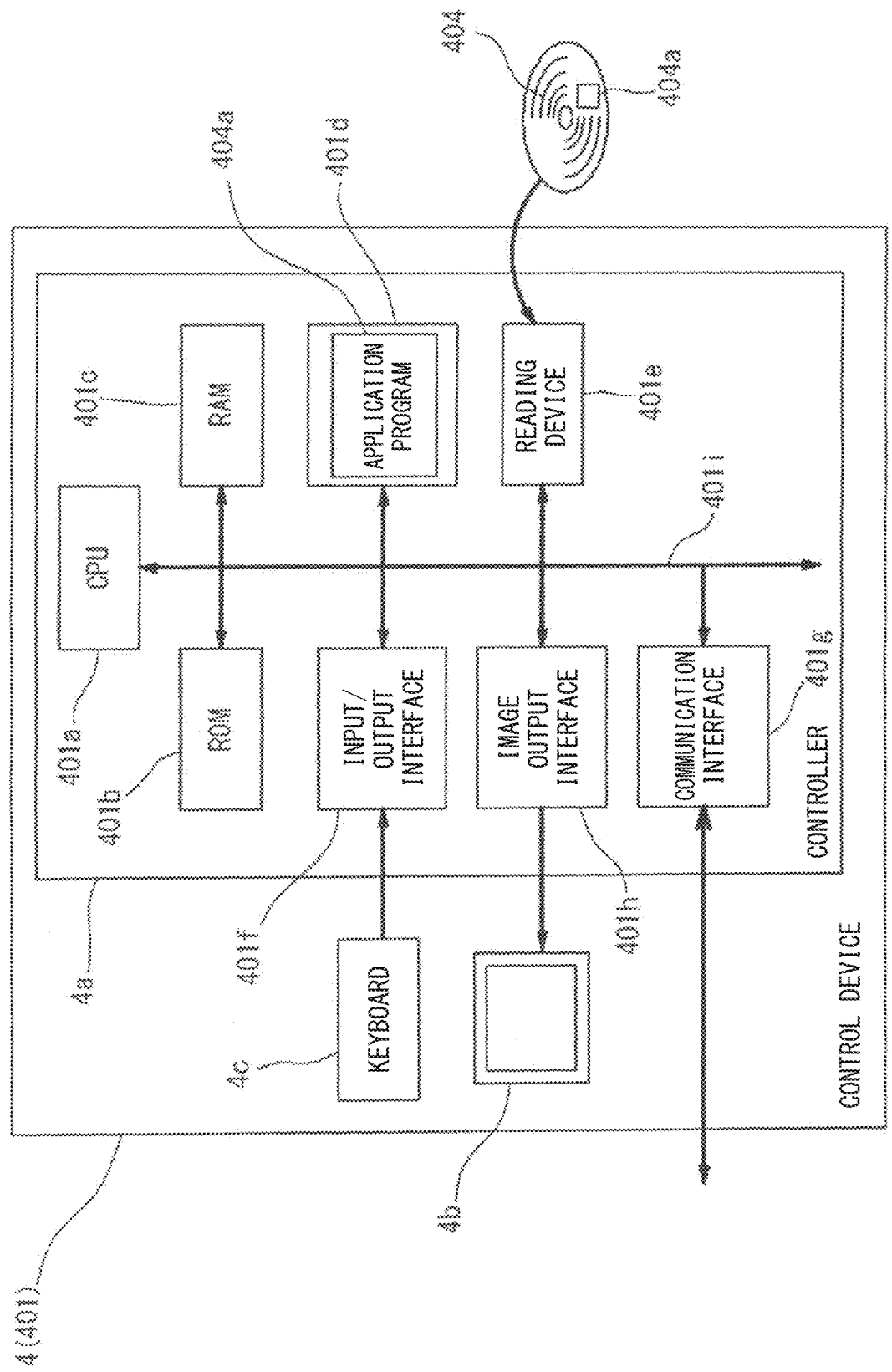
FIG. 7 illustrates a configuration of a control device of the blood specimen analyzer.

With reference to FIG. 7, the controller 4a mainly includes a CPU 401a, a ROM 401b, a RAM 401c, a hard disk 401d, a reading device 401e, an input/output interface 401f, a communication interface 401g, and an image output interface 401h. The CPU 401a, the ROM 401b, the RAM 401c, the hard disk 401d, the reading device 401e, the input/output interface 401f, the communication interface 401g, and the image output interface 401h are connected by a bus 401i.

The CPU 401a can execute a computer program stored in the ROM 401b and a computer program which has been loaded to the RAM 401c. The ROM 401b includes a mask ROM, PROM, EPROM, EEPROM, and the like. In the ROM 401b, for example, the computer program executed by the CPU 401a and data used for the computer program are stored.

The RAM 401c includes an SRAM, a DRAM, or the like. The RAM 401c is used for reading the computer program stored in the ROM 401b and the hard disk 401d. The RAM 401c is used as a work area for the CPU 401a when the computer program is executed.

In the hard disk 401d, an operating system, a computer program such as an application program (computer program for analyzing a blood specimen) to be executed by the CPU 401a, data used for execution of the computer program, and contents of setting for the control device 4 are installed.

The reading device 401e is implemented by a flexible disk drive, a CD-ROM drive, a DVD-ROM drive, or the like, and can read a computer program or data stored in a portable storage medium 404.

The input/output interface 401f includes, for example, a serial interface such as USB, IEEE1394, and RS-232C, a parallel interface such as SCSI, IDE, and IEEE1284, and an analog interface such as a D/A converter and an A/D converter. The keyboard 4c is connected to the input/output interface 401f, and a user is allowed to input data to the computer 401 by using the keyboard 4c.

The communication interface 401g is, for example, an Ethernet (registered trademark) interface. The computer 401 can transmit data to and receive data from the measurement unit 2 through the communication interface 401g by using a predetermined communication protocol.

The image output interface 401h is connected to the display unit 4b which is implemented by a LCD, a CRT, or the like, and outputs, to the display unit 4b, a video signal corresponding to image data provided by the CPU 401a. The display unit 4b displays an image (screen) according to the inputted video signal.

The control device 4 functions as means for obtaining a coagulation waveform based on optical information (for example, transmitted light intensity) detected by the detection unit 80. In a blood specimen analyzer according to a third mode, the control device 4 functions as an information obtaining unit for obtaining information concerning an amount of antigen of fibrinogen, based on the coagulation waveform. In a blood specimen analyzer according to a fourth mode, the control device 4 functions as an information obtaining unit for obtaining information concerning a function of fibrinogen based on the coagulation waveform. In the blood specimen analyzer according to the fourth mode, the control device 4 may function as an information obtaining unit that obtains information concerning an amount of antigen of fibrinogen and information concerning an active concentration of fibrinogen based on the coagulation waveform, and that obtains information concerning a ratio between the amount of antigen of fibrinogen and the activity based on the obtained information. Furthermore, in the blood specimen analyzer according to the fourth mode, the control device 4 may function as an information obtaining unit that obtains information concerning an amount of antigen of fibrinogen and information concerning an active concentration of fibrinogen based on the coagulation waveform, and that obtains information concerning abnormality in fibrinogen based on the obtained information.

(Procedure of Process by Blood Specimen Analyzer)

Figure 9:
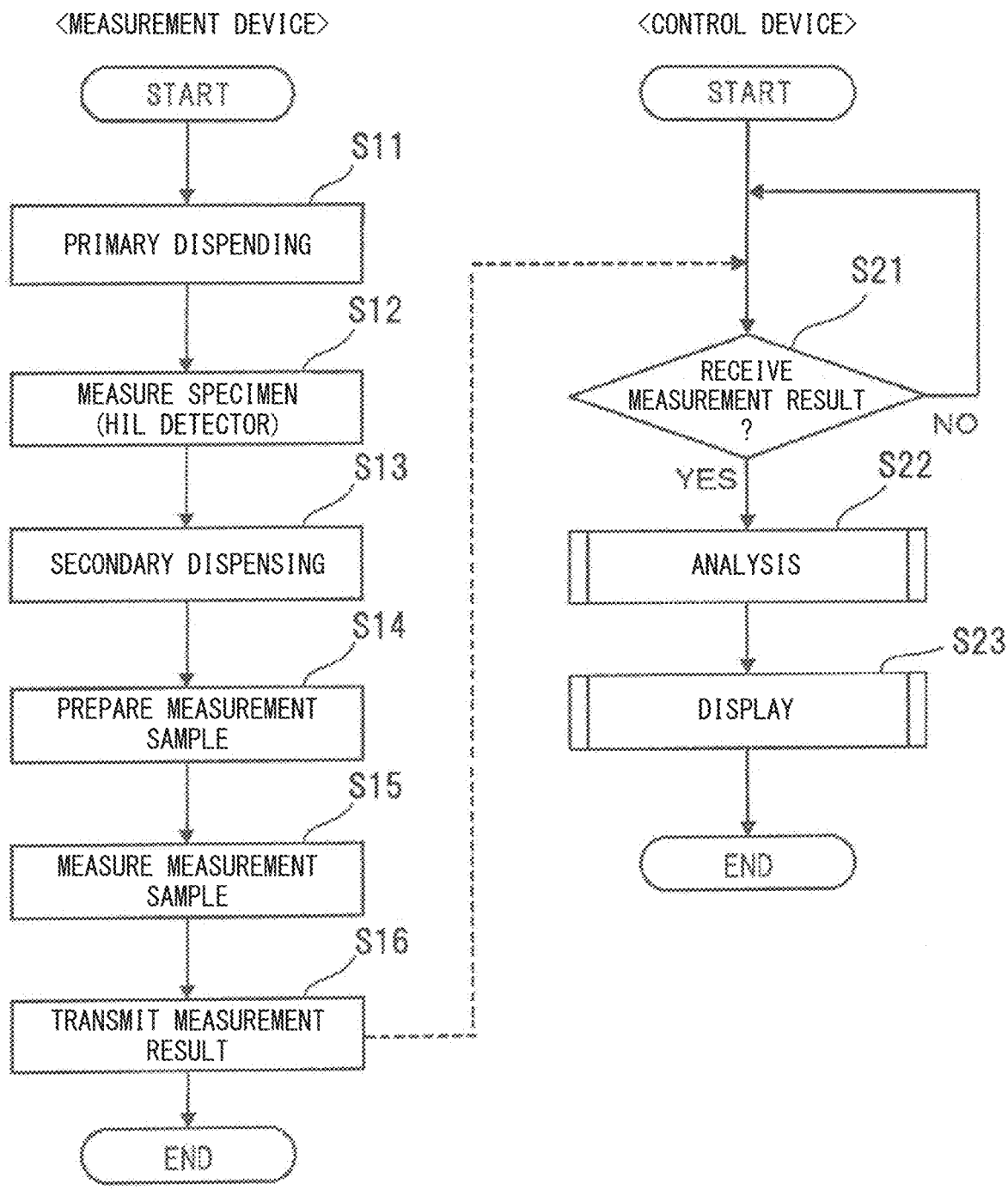
FIG. 9 is a flow chart showing measurement of a blood specimen by the blood specimen analyzer.

The measurement device 5 performs processing mainly under the control of the controller 120, and the control device 4 performs processing mainly under the control of the controller 4a. When receiving, from the control device 4, an instruction inputted by a user for starting measurement, the measurement device 5 starts the measurement. With reference to FIG. 9, when the measurement is started, a predetermined amount of blood specimen is aspirated from the test tube 150 by the specimen dispensing arm 30. The specimen dispensing arm 30 is moved to a portion above the cuvette 152 held by the primary dispensing table 24 of the rotary transport unit 20. After that, the predetermined amount of blood specimen is discharged into the cuvette 152 in the primary dispensing table 24, by the specimen dispensing arm 30, thereby primarily dispensing the blood specimen into the cuvette 152 (step S11).

The primary dispensing table 24 is rotated, and the cuvette 152 into which the specimen has been dispensed is transported to a position at which measurement can be performed by the HIL detector 40, and the blood specimen is optically measured by the HIL detector 40 (step S12). A predetermined amount of blood specimen is aspirated from the cuvette 152 held by the holding portion 24a of the primary dispensing table 24, by the specimen dispensing arm 30. After that, the predetermined amount of blood specimen is discharged into the cuvette 152 in the secondary dispensing table 23 by the specimen dispensing arm 30, thereby secondarily dispensing the blood specimen into the cuvette 152 (step S13).

The reagent dispensing arms 60 are driven to add a thrombin-containing reagent in the reagent containers (not shown) placed in the reagent tables 21 and 22 to the blood specimen in the cuvettes 152 in the secondary dispensing table 23. Thus, the measurement sample is prepared (step S14). The cuvette 152, in the secondary dispensing table 23, which contains the measurement sample is moved into the insertion hole 81a of the cuvette setting portion 81 of the detection unit 80 by using the cuvette transfer unit 70.

The detector 82 of the detection unit 80 optically measures the measurement sample in the cuvette 152 (step S15). In this measurement, light is applied by the light source 82a, and light that has been transmitted through the measurement sample in the cuvette 152 is received by the photoelectric conversion element 82b, and is converted to an electrical signal corresponding to an amount of the transmitted light (transmitted light intensity). The electrical signal is converted to a digital signal by a not-illustrated A/D converter. The measurement result is obtained as data in which an amount of transmitted light per a predetermined time is associated with a time when each amount of the transmitted light is measured. The controller 120 of the measurement device 5 causes the measurement result to be transmitted to the control device 4 (step S16).

When the control device 4 receives the measurement result (data) from the measurement device 5 (step S21: YES), the control device 4 executes analysis of the received measurement result (step S22). The controller 4a generates, from the obtained data, a coagulation reaction curve (coagulation waveform) that represents change of the transmitted light intensity according to elapse of time. With reference to FIG. 1, when the measurement is started immediately after addition of the reagent, change of the transmitted light intensity is little. After that, as the coagulation progresses, the measurement sample is clouded, and the transmitted light intensity is rapidly reduced. When the coagulation reaction is almost ended, change of the transmitted light intensity becomes slight, and the intensity then becomes almost constant.

In a case where the transmitted light intensity (starting level) at the start of the coagulation reaction is 0%, and an amount of transmitted light (ending level) at a time when the transmitted light intensity no longer changes is 100%, the controller 4a obtains, from the coagulation waveform, a time t when a predetermined detection percent (for example, 50%) is reached, and obtains the time t as the coagulation time. The starting level represents the maximum transmitted light intensity during a predetermined time (for example, 60 seconds) after addition of the reagent. The ending level represents an amount of transmitted light at a time when an amount of reduction of the transmitted light intensity per a predetermined time is less than or equal to a predetermined value after the time when the starting level is recognized. The control device 4 obtains, from the generated coagulation waveform, a value of a parameter concerning differentiation of the coagulation waveform, and the total reaction time. After the analysis, the control device 4 causes the result of the analysis to be displayed (step S23).

(Procedure of Process for Obtaining Information Concerning Amount of Antigen of Fibrinogen)

Figure 10A:
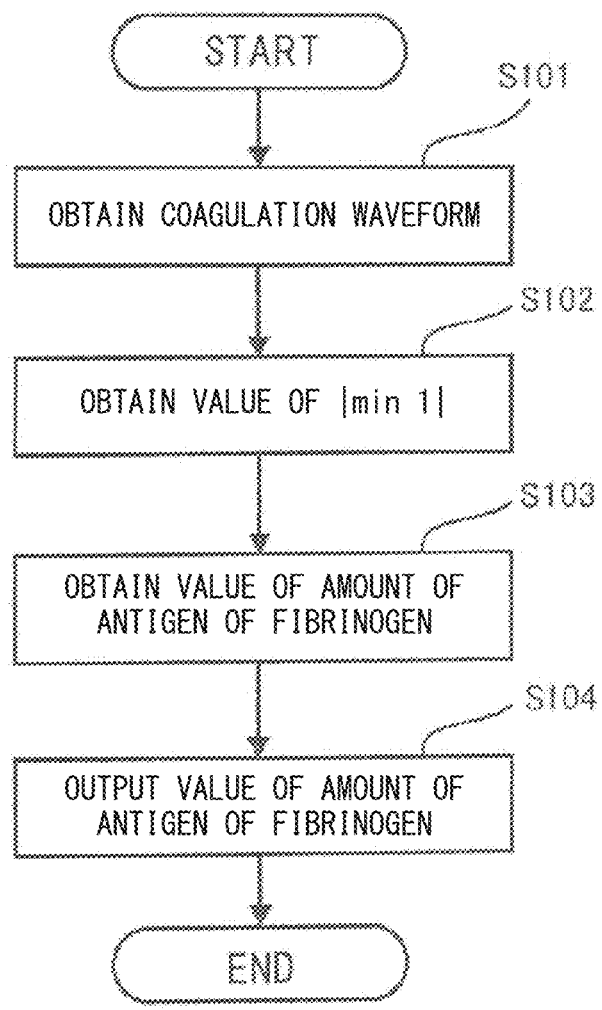
FIG. 10A is a flow chart showing analysis of a blood specimen by the blood specimen analyzer.

A flow of a process for obtaining information concerning an amount of antigen of fibrinogen will be described with reference to FIG. 10A. An exemplary case where a value of |min 1| is obtained from the coagulation waveform, and, from the obtained value, a value of an amount of antigen of fibrinogen in the blood specimen is obtained, will be described. However, the present embodiment is not limited to this exemplary case. In this example, |max 2| or the total reaction time may be obtained instead of |min 1|.

In step S101, the CPU 401a of the control device 4 obtains the coagulation waveform of the transmitted light intensity based on the data received from the measurement device 5. Next, in step S102, the CPU 401a calculates, from the obtained coagulation waveform, a value of |min 1| according to the expression, for calculating a parameter concerning differentiation of the coagulation waveform, which is stored in the hard disk 401d. In step S103, the CPU 401a calculates, from the calculated value of |min 1|, a value of an amount of antigen of fibrinogen according to a conversion expression stored in the hard disk 401d. The conversion expression is generated in advance by measuring normal plasma and stored in the hard disk 401d of the controller 4a. In step S104, the CPU 401a causes the obtained value of the amount of antigen of fibrinogen to be transmitted to the image output interface 401h. The image output interface 401h causes the display unit 41 to display the value of the amount of antigen of fibrinogen or causes a printer to print the value. Alternatively, the value may be outputted by sound. Thus, the value of an amount of antigen of fibrinogen can be provided to a user as, for example, an estimated amount of antigen.

(Procedure of Process for Obtaining Information Concerning Ratio Between Amount of Antigen of Fibrinogen, and Activity)

Figure 10B:
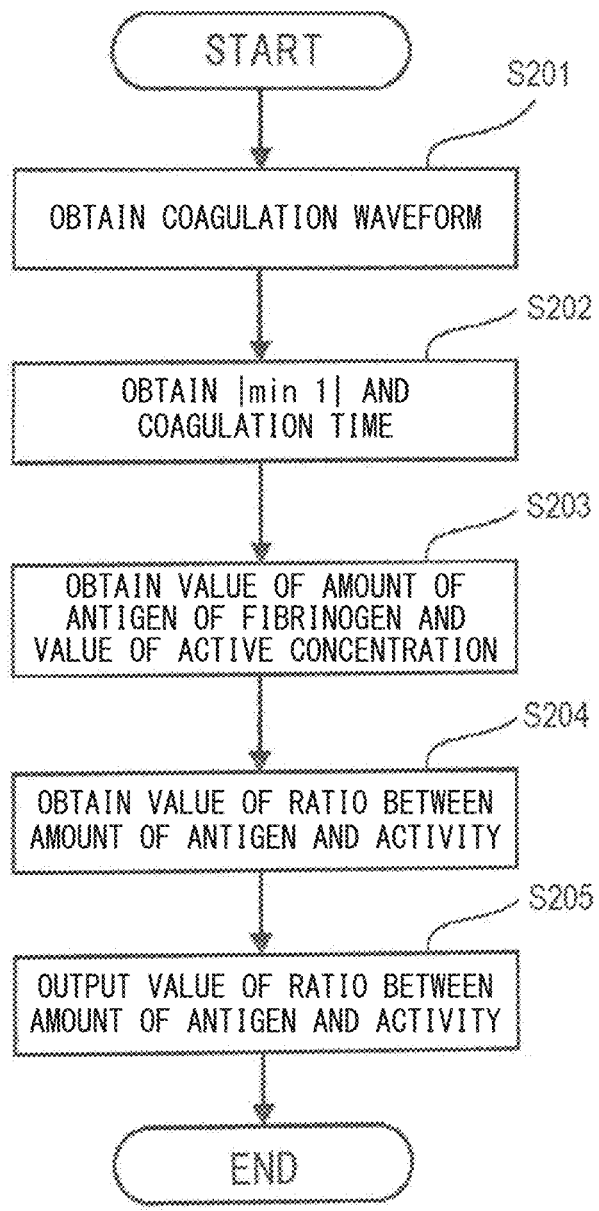
FIG. 10B is a flow chart showing analysis of a blood specimen by the blood specimen analyzer.

A flow of a process for obtaining information concerning a ratio between an amount of antigen and the activity will be described with reference to FIG. 10B. An exemplary case where a value of |min 1| and a coagulation time are obtained from a coagulation waveform, and, from the obtained values, a value of a ratio between an amount of antigen and the activity of a blood specimen is obtained, will be described. However, the present embodiment is not limited to this exemplary case. In this example, |max 2| or the total reaction time may be obtained instead of |min 1|. The value of the ratio between an amount of antigen and the activity may be obtained according to expression (2) described above instead of expression (1) described above.

In step S201, the CPU 401a of the control device 4 obtains a coagulation waveform of a transmitted light intensity, based on data received from the measurement device 5. Next, in step S202, the CPU 401a calculates, from the obtained coagulation waveform, a value of |min 1| according to expressions, stored in the hard disk 401d, for calculating a parameter concerning differentiation of a coagulation waveform, and a coagulation time. The CPU 401a obtains a coagulation time from the obtained coagulation waveform. In step S203, the CPU 401a calculates a value of an amount of antigen of fibrinogen from the value of |min 1| as in step S103 described above. The CPU 401a calculates a value of an active concentration of fibrinogen from the calculated value of the coagulation time according to the conversion expression stored in the hard disk 401d. The conversion expression is generated in advance by measuring a thrombin standard solution the concentration of which is known, and is stored in the hard disk 401d of the controller 4a.

In step S204, the CPU 401a obtains a value of a ratio between an amount of antigen and an activity, from the obtained value of the amount of antigen of fibrinogen and the obtained value of the active concentration, according to the above-described expression (1) stored in the hard disk 401d. In step S204, the CPU 401a causes the value of the ratio between the amount of antigen and the activity to be transmitted to the image output interface 401h. The image output interface 401h causes the display unit 41 to display the value of the ratio between the amount of antigen and the activity, or causes the printer to print the value. Alternatively, the value may be outputted by sound. The value of the amount of antigen of fibrinogen and the value of the active concentration may be also displayed by the display unit 41. Thus, the value of the ratio between the amount of antigen and the activity can be provided to a user as, for example, a specific activity.

(Procedure of Process for Obtaining Information Concerning Abnormality in Fibrinogen)

Figure 10C:
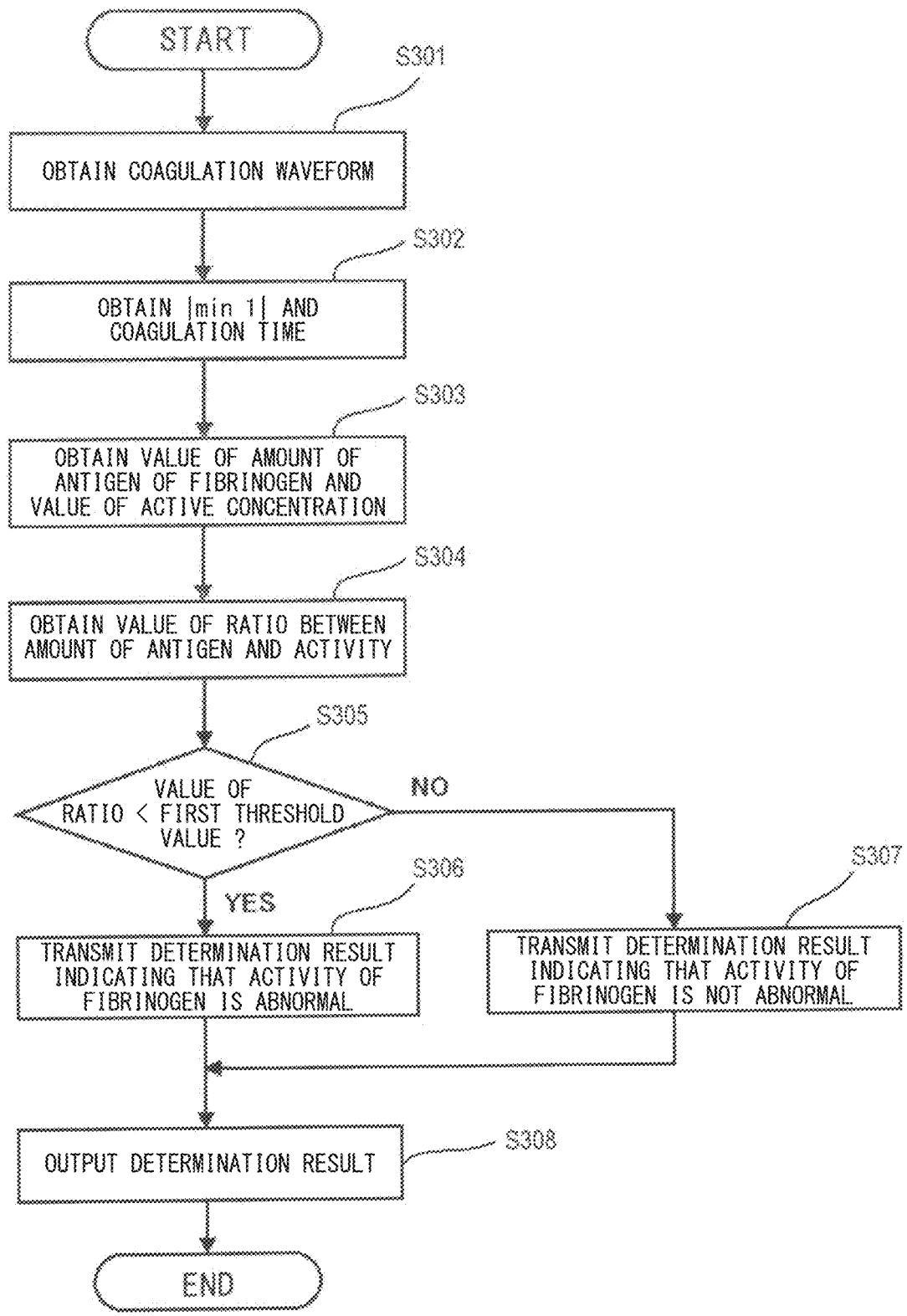
FIG. 10C is a flow chart showing analysis of a blood specimen by the blood specimen analyzer.

A flow of a process for obtaining information concerning abnormality in fibrinogen will be described with reference to FIG. 10C. An exemplary case where a value of |min 1| and a coagulation time are obtained from a coagulation waveform, a value of a ratio between an amount of antigen of fibrinogen and an activity in a blood specimen is obtained from the obtained values, and information concerning abnormality of the activity of fibrinogen is obtained based on the value of the ratio, will be described. However, the present embodiment is not limited to this example. In this example, |max 2| or the total reaction time may be obtained instead of |min 1|. The value of the ratio between an amount of antigen of fibrinogen and an activity may obtained according to expression (2) described above instead of expression (1) described above.

Steps S301 to S304 are similar to steps S201 to S204, respectively, described above. In step S305, the CPU 401a determines whether or not the activity of fibrinogen is abnormal, by using the obtained value of the ratio, and the first threshold value stored in the hard disk 401d. When the value of the ratio is less than the first threshold value, the process is advanced to step S306. In step S306, the CPU 401a causes a determination result indicating that the activity of fibrinogen is abnormal to be transmitted to the image output interface 401h. Meanwhile, when the value of the ratio is not less than the first threshold value (that is, the value of the ratio is greater than or equal to the first threshold value), the process is advanced to step S307. In step S307, the CPU 401a causes the determination result indicating that the activity of fibrinogen is not abnormal to be transmitted to the image output interface 401h.

In a case where the value of the ratio is calculated according to expression (2) described above, the value of the ratio and the second threshold value are compared with each other. At this time, when the value of the ratio is less than the second threshold value or when the value of the ratio is equal to the second threshold value, the CPU 401a causes the determination result indicating that the activity of fibrinogen is not abnormal to be transmitted to the image output interface 401h. When the value of the ratio is greater than the second threshold value, the CPU 401a causes the determination result indicating that the activity of fibrinogen is abnormal to be transmitted to the image output interface 401h.

In step S308, the image output interface 401h causes the display unit 41 to display the information concerning abnormality of a function of fibrinogen or causes the printer to print the information. Alternatively, the information may be outputted by sound. The value of the amount of antigen of fibrinogen and the value of the active concentration, and the value of the ratio between the value of the amount of antigen of fibrinogen and the value of the active concentration may be also displayed by the display unit 41.

Figure 11:
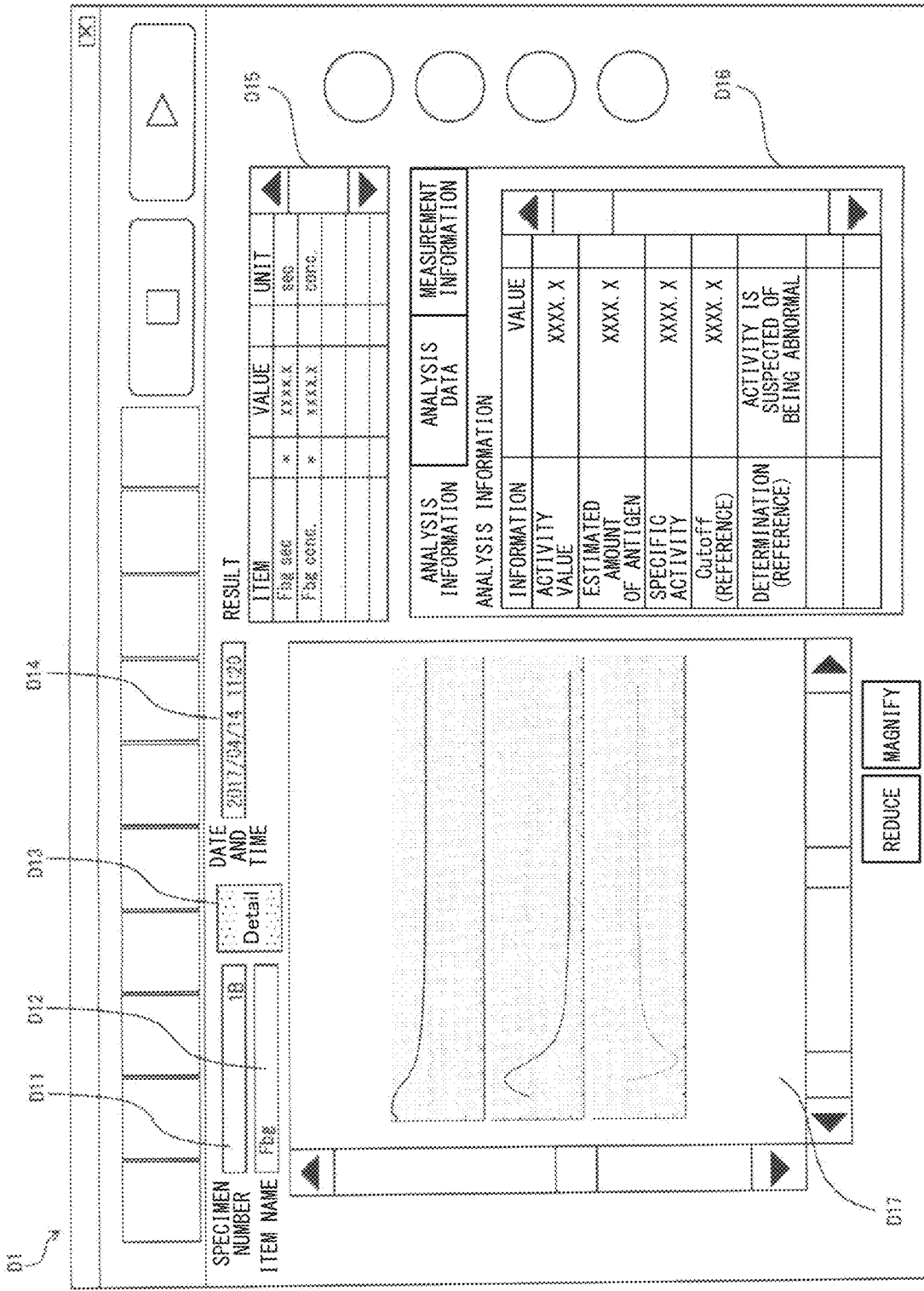
FIG. 11 illustrates an example of a screen on which a result of analysis by the blood specimen analyzer is displayed.

An example of a screen on which the result of the analysis is displayed will be described with reference to FIG. 11. A screen D1 includes a region D11 in which a specimen number is displayed, a region D12 in which a measurement item name is displayed, a button D13 for displaying a detailed screen, a region D14 in which measurement date and time are displayed, a region D15 in which a measurement result is displayed, a region D16 in which analysis information is displayed, and a region D17 in which a coagulation waveform, and a graph obtained by differentiation of the coagulation waveform are displayed.

In the region D15, the measurement item and the measured value are displayed. In the region D15, "Fbg sec" represents a coagulation time according to the thrombin time method. "Fbg conc." represents an active concentration of fibrinogen. In the region D15, a value of the differentiation parameter such as |min 1| or the total reaction time may be displayed.

In the region D16, an analysis item and reference information are displayed. In the region D16, "activity value" represents a value of the active concentration of fibrinogen. "Estimated amount of antigen" represents a value of an amount of antigen of fibrinogen, which is obtained based on the value of the differentiation parameter or the total reaction time. "Specific activity" represents a value of a ratio between an amount of antigen and an activity (value of active concentration of fibrinogen/value of an amount of antigen of fibrinogen). "Cutoff (reference)" represents a normal value (first threshold value) for the value of the specific activity. "Determination (reference)" represents a result of determination by the blood specimen analyzer. FIG. 11 shows a blood specimen that is suspected of being abnormal in activity of fibrinogen. The diagnosis of the abnormality in fibrinogen is preferably performed in consideration of information such as another test result as well as based on the determination result. Therefore, "(reference)" is indicated in order to indicate that Cutoff and the determination result by the blood specimen analyzer according to the present embodiment, are reference information. In FIG. 11, the determination result is indicated by characters as "activity is suspected to be abnormal". However, the determination result may be indicated as a pictorial mark or a symbol such as a flag. Alternatively, the determination result may be outputted by sound.

Hereinafter, the present invention will be described in more detail according to examples. However, the present invention is not limited to these examples.

EXAMPLES

Example 1: Correlation Between: Amount of Antigen of Fibrinogen; and Differentiation Parameter and Total Reaction Time (1) Obtaining a Value of a Parameter Concerning Differentiation of a Coagulation Waveform and a Total Reaction Time Coagulation waveforms of normal plasma (12 specimens) were measured by using Thrombocheck Fib (L) (SYSMEX CORPORATION) as a fibrinogen kit. The kit was based on the thrombin time method, and contained a thrombin-containing reagent. Specific operation was performed according to a manual attached to the kit. The measurement was performed by using CS-5100 of the automatic blood coagulation measurement device (SYSMEX CORPORATION). Change of the transmitted light intensity in each specimen to which the thrombin-containing reagent was added, was measured by CS-5100 with elapse of time, to obtain a coagulation waveform. Furthermore, |min 1|, |max 2|, and the total reaction time of each specimen were obtained by CS-5100.

(2) Measuring an Amount of Antigen of Fibrinogen

An amount of antigen of fibrinogen in the normal plasma was measured in a latex agglutination method by using Factor Auto (registered trademark) Fibrinogen (Q-may Laboratory Corporation) as a kit for measuring fibrinogen in plasma. The kit includes anti-fibrinogen antibody. Specific operation was performed according to a manual attached to the kit.

Figure 12A:
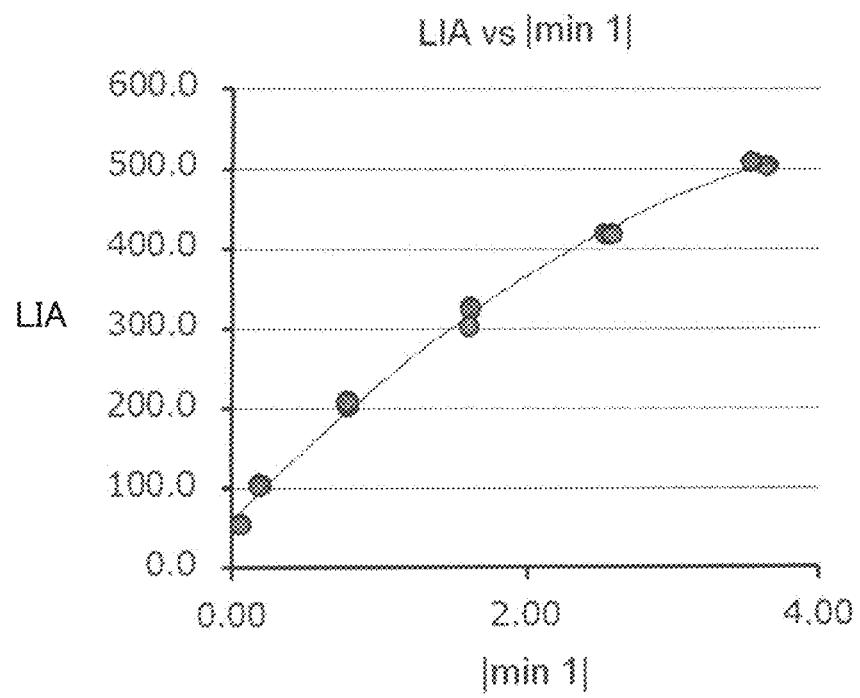
FIG. 12A is a graph showing correlation between |min 1| and an amount of antigen of fibrinogen measured by latex immunoassay (LIA), for normal plasma.
Figure 12B:
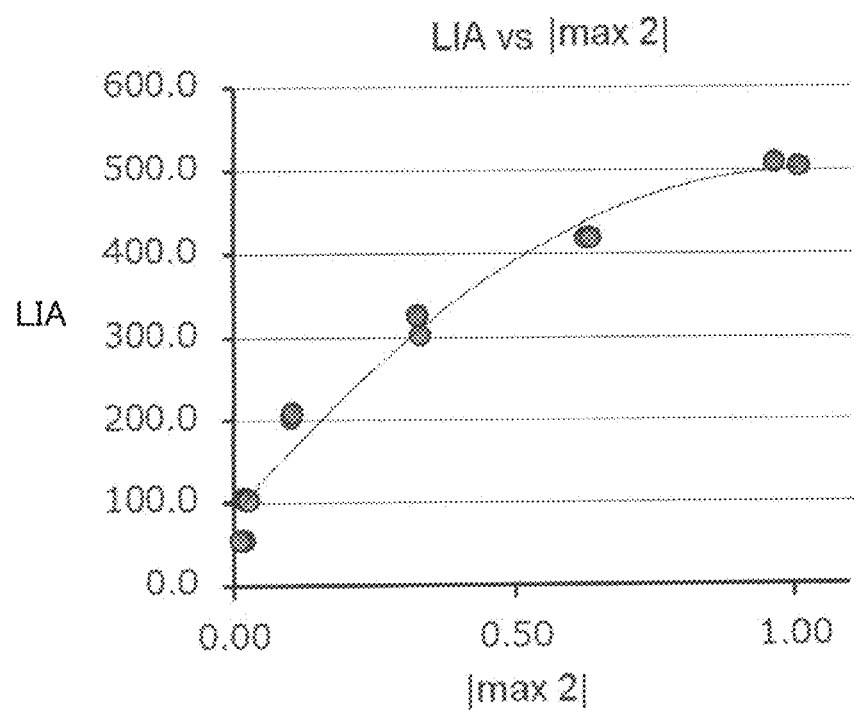
FIG. 12B is a graph showing correlation between |max 2| and an amount of antigen of fibrinogen measured by LIA, for normal plasma.
Figure 12C:
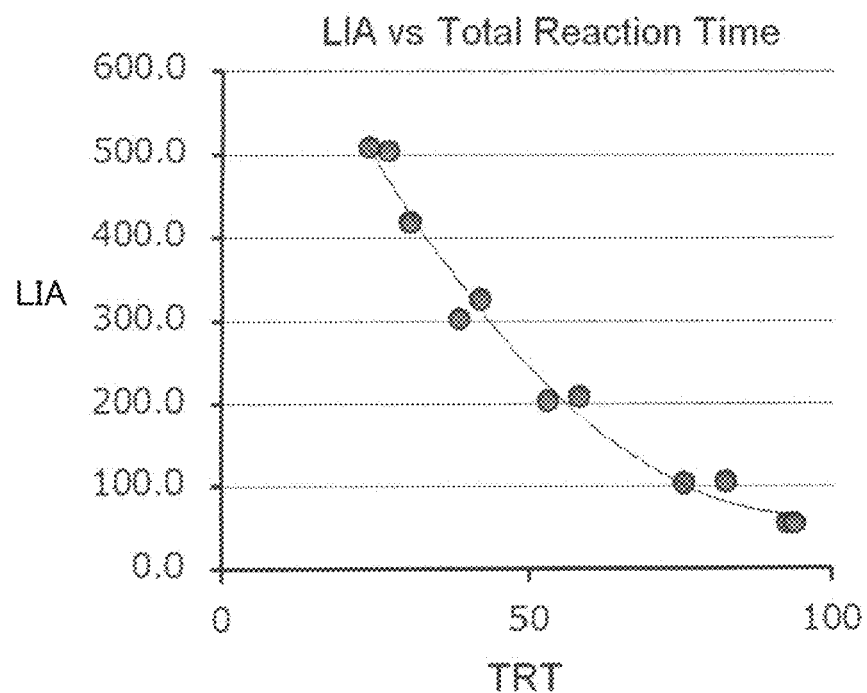
FIG. 12C is a graph showing correlation between a total reaction time, and an amount of antigen of fibrinogen measured by LIA, for normal plasma.
Figure 13A:
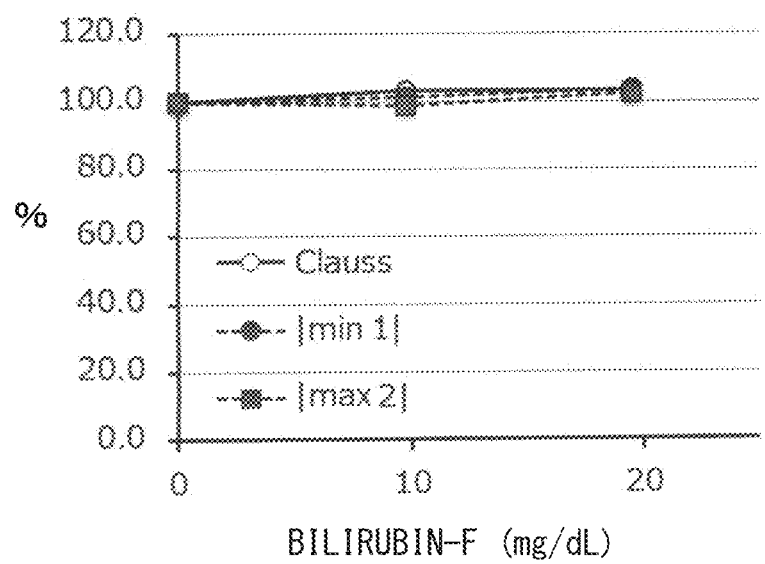
FIG. 13A is a graph showing change of values of an active concentration (Clauss), |min 1|, and |max 2| in a specimen containing bilirubin-F.
Figure 13B:
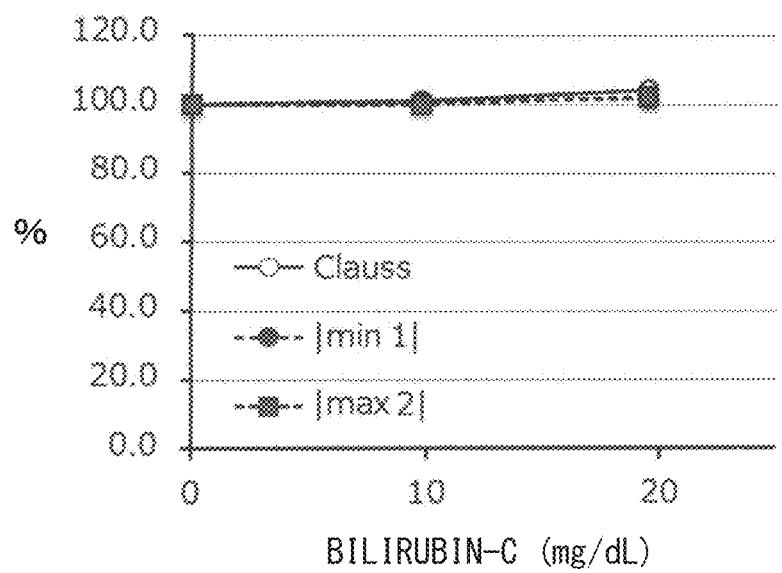
FIG. 13B is a graph showing change of values of an active concentration (Clauss), |min 1|, and |max 2| in a specimen containing bilirubin-C.
Figure 13C:
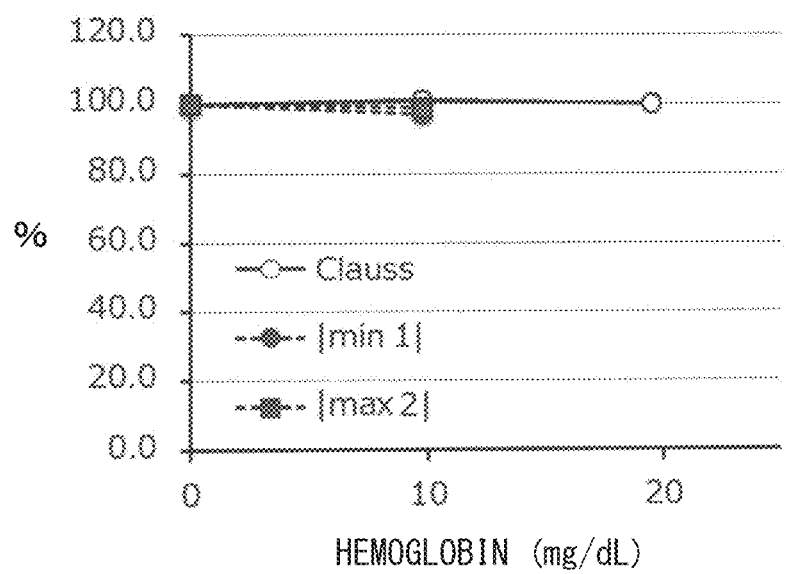
FIG. 13C is a graph showing change of values of an active concentration (Clauss), |min 1|, and |max 2| in a specimen containing hemoglobin.
Figure 13D:
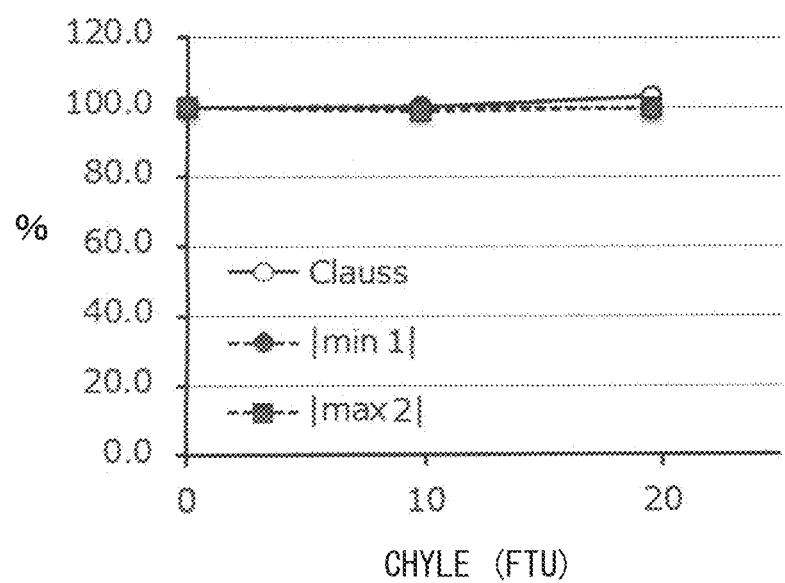
FIG. 13D is a graph showing change of values of an active concentration (Clauss), |min 1|, and |max 2| in a specimen containing chyle.

(3) Correlation Between: An Amount of Antigen of Fibrinogen; and a Differentiation Parameter and a Total Reaction Time The amount of antigen of fibrinogen and the coagulation waveform parameters of each specimen were plotted to generate graphs. In each graph, the regression equation was generated to calculate a coefficient of determination ($R^2$). The results are indicated in FIGS. 12A to 12C and Table 1. In FIGS. 12A to 12C and Table 1, LIA represents latex immunoassay, and TRT represents a total reaction time.

TABLE 1

| | Regression equation | Coefficient of determination ($R^2$) |
|---|---|---|
| LIA vs |min 1| | y = $-18.438x^2 + 190.3x + 59.237$ | 0.9961 |
| LIA vs |max 2| | y = $-397.64x^2 + 814.16x + 84.442$ | 0.9728 |
| LIA vs TRT | y = $0.0837x^2 - 16.138x + 843.35$ | 0.9834 |

As indicated in FIGS. 12A to 12C and Table 1, each of |min 1|, |max 2|, and the total reaction time is well correlated with an amount of antigen of fibrinogen measured in the latex agglutination method. Therefore, by using the obtained graph or regression equation, |min 1|, |max 2|, and the total reaction time can be converted to an amount of antigen of fibrinogen. Thus, it has been indicated that information concerning an amount of antigen of fibrinogen can be obtained from |min 1|, |max 2|, and the total reaction time.

Example 2: Determination of Fibrinogen Disorder Based on Coagulation Waveform Analysis (1) Calculation of Threshold Value A conversion value of an amount of antigen of fibrinogen was obtained from |min 1| of normal plasma by using the regression equation obtained in Example 1. Hereinafter, a conversion value obtained from a coagulation waveform parameter is also referred to as an "estimated amount of antigen" or "eAg". An active concentration of fibrinogen in normal plasma was obtained from a coagulation time measured in Example 1, by using a calibration curve generated by measuring a coagulation time of a fibrinogen standard solution the concentration of which was known. Hereinafter, a value of the active concentration of fibrinogen is also referred to as "Ac". A ratio (Ac/eAg) of the active concentration of fibrinogen to the estimated amount of antigen was calculated with respect to |min 1| of the normal plasma. The obtained value (mean±2SD) of Ac/eAg was 1.103±0.305. In Example 2, the value of the ratio was used as a predetermined threshold value.

(2) Measurement of Specimen of Patient

Coagulation waveforms were measured for plasma (4 specimens) obtained from patients diagnosed as fibrinogen disorder, by the thrombin time method, in the same manner as in Example 1, to obtain |min 1|. An amount of antigen of fibrinogen was measured in the latex agglutination method for the plasma in the same manner as in Example 1. Hereinafter, a value of an amount of antigen of fibrinogen which was obtained in the latex agglutination method is also referred to as "Ag". In the same manner as in (1) described above, for the specimen of each patient, Ac was obtained from the coagulation time and eAg was obtained from |min 1|, to calculate Ac/eAg. The results are indicated in Table 2.

TABLE 2

| | Ac (mg/dL) | Ag (mg/dL) | |min 1| | eAg (mg/dL) | Ac/eAg |
|---|---|---|---|---|---|
| Patient 1 | 48.8 | 111.0 | 0.1080 | 79.6 | 0.613 |
| Patient 2 | 32.3 | 451.5 | 0.2861 | 112.2 | 0.287 |
| Patient 3 | 55.7 | 130.7 | 0.1357 | 84.7 | 0.657 |
| Patient 4 | 145.3 | 314.8 | 0.8940 | 214.6 | 0.677 |

(3) Results

Fibrinogen disorder is a disease in which, although an amount of protein of fibrinogen is not abnormal, the activity of fibrinogen is abnormal. Therefore, in the blood specimen of fibrinogen disorder, although an amount of antigen of fibrinogen is normal, the active concentration of fibrinogen indicates a small value. In practice, as indicated in Table 2, in plasma of each of the patients 1 to 4, the active concentration (Ac) of fibrinogen is reduced as compared to a value of an amount of antigen (Ag). This can be said from the comparison between an estimated amount of antigen (eAg) and the active concentration (Ac) of fibrinogen. The value of Ac/eAg of each of the patients 1 to 4 was significantly less than the predetermined threshold value (Ac/eAg of normal plasma) obtained in (1) described above ($p<0.00001$). This indicates that a ratio between the active concentration of fibrinogen and an amount of antigen of fibrinogen based on differentiation parameter is useful as a new index concerning the function of fibrinogen. It has been indicated that, by comparison between the value of the ratio for the specimen and the value of the ratio for the normal specimen, abnormality of activity of fibrinogen can be determined.

Example 3: Determination (2) of Fibrinogen Disorder Based on Coagulation Waveform Analysis (1) Calculation of Threshold Value An estimated amount of antigen (eAg) of fibrinogen was obtained from |max 2| and the total reaction time of normal plasma by using the regression equation obtained in Example 1. Ac/eAg was calculated with respect to each of |max 2| and the total reaction time of normal plasma by using the active concentration (Ac) of fibrinogen in the normal plasma obtained in Example 2. The value (mean±2SD) of Ac/eAg by |max 2| of the normal plasma was 1.171±0.259. The value (mean±2SD) of Ac/eAg by the total reaction time of the normal plasma was 0.678±0.368. In Example 3, these values of the ratios were each used as a predetermined threshold value.

(2) Measurement of Specimen of Patient

The values of Ac and Ag of specimen of each patient were the same as in example 2. A coagulation waveform was measured for the plasma of each of the patients 1 to 3 of example 2 in the thrombin time method in the same manner in Example 1, to obtain |max 2| and the total reaction time. eAg was obtained from each of |max 2| and the total reaction time by using the regression equation obtained in Example 1, to calculate Ac/eAg. The results are indicated in Tables 3 and 4.

TABLE 3

| | Ac (mg/dL) | Ag (mg/dL) | |max 2| | eAg (mg/dL) | Ac/eAg |
|---|---|---|---|---|---|
| Patient 1 | 48.8 | 111.0 | 0.0244 | 104.1 | 0.468 |
| Patient 2 | 32.3 | 451.5 | 0.0199 | 100.5 | 0.320 |
| Patient 3 | 55.7 | 130.7 | 0.0610 | 102.3 | 0.544 |

TABLE 4

| | Ac (mg/dL) | Ag (mg/dL) | TRT | eAg (mg/dL) | Ac/eAg |
|---|---|---|---|---|---|
| Patient 1 | 48.8 | 111.0 | 137.37 | 205.9 | 0.237 |
| Patient 2 | 32.3 | 451.5 | 144.33 | 257.7 | 0.125 |
| Patient 3 | 55.7 | 130.7 | 136.23 | 198.2 | 0.281 |

(3) Results

The value of Ac/eAg by |max 2| of each of the patients 1 to 3 was less than the predetermined threshold value obtained by |max 2| in (1) described above. The value of Ac/eAg, by the total reaction time, of each of the patients 1 to 3 was significantly less than the predetermined threshold value obtained by the total reaction time in (1) described above ($p<0.00001$). This indicates that a ratio between the active concentration of fibrinogen and an amount of antigen of fibrinogen based on the differentiation parameter or the total reaction time can be used as an index concerning the function of fibrinogen, also with respect to |max 2| and the total reaction time, similarly to |max 1|. It is indicated that, by comparison between the value of the ratio for the specimen and the value of the ratio for the normal specimen, abnormality of the activity of fibrinogen can be determined.

Reference Example: Influence of Interference Substance in Obtaining of Parameter Concerning Differentiation of Coagulation Waveform (1) Preparation of Specimen Containing Interference Substance Bilirubin-F (final concentration of 0, 10, or 20 mg/dL), bilirubin-C (final concentration of 0, 10, or 20 mg/dL), hemoglobin (final concentration of 0, 10, or 20 mg/dL), or chyle (final concentration of 0, 10, or 20 FTU) was added to normal plasma, to prepare a specimen containing an interference substance.

(2) Measurement of Specimen

A coagulation waveform was measured for the above-described specimen in the thrombin time method as in Example 1, to obtain a coagulation time, |min 1|, and |max 2|. A calibration curve generated by measuring a coagulation time of a fibrinogen standard solution the concentration of which was known, was used to obtain an active concentration of fibrinogen from the coagulation time of each specimen. Values of the active concentration, |min 1|, and |max 2| obtained from a specimen (final concentration of 0 mg/dL or 0 FTU) containing no interference substance were each set as 100%, and change of the active concentration, |min 1|, and |max 2| obtained from the specimen containing the interference substance was calculated. The results are indicated in FIGS. 13A to 13D. In FIGS. 13A to 13D, "Clauss" represents an active concentration of fibrinogen.

As shown in FIGS. 13A to 13D, a value of a parameter concerning differentiation of the coagulation waveform, and the active concentration of fibrinogen, which were obtained from the specimen containing the interference substance, are almost equal to values obtained from the specimen containing no interference substance. Accordingly, it is indicated that the analyzing method of the present embodiment is not influenced by an interference substance.

What is claimed is:

1. An analyzing method for analyzing a blood specimen, the analyzing method comprising:
    mixing a blood specimen and a thrombin-containing reagent to coagulate the blood specimen, and obtaining a coagulation waveform comprised of values of an optical parameter versus time measured on the blood specimen as the blood specimen coagulates after the blood specimen and the thrombin-containing reagent are mixed;
    obtaining a value of a parameter concerning differentiation of the coagulation waveform or a total reaction time that is a length of time beginning from when the blood specimen and the thrombin-containing reagent are mixed and up to a time when a measurement value of the coagulation waveform no longer changes, based on the coagulation waveform, wherein the parameter concerning the differentiation of the coagulation waveform is at least one selected from a maximum coagulation speed (|min 1|) or a maximum coagulation deceleration (|max 2|); and
    obtaining a Quantitative or Qualitative information concerning an estimated amount of antigen of fibrinogen in the blood specimen based on the obtained value of the parameter or the total reaction time using a calibration curve or a regression equation of the calibration curve, wherein the estimated amount of antigen of fibrinogen correlates to an amount of antigen of fibrinogen in the blood specimen obtained by immunological measurement using an anti-fibrinogen antibody, and wherein the calibration curve is created based on plots of the differentiation parameter or total reaction time vs. an amount of antigen of fibrinogen determined by the immunological measurement for a plurality of normal specimens.

2. The analyzing method of claim 1, wherein the quantitative information concerning an amount of antigen of fibrinogen is a value of an amount of antigen of fibrinogen.

3. The analyzing method, for analyzing a blood specimen, of claim 1, further comprising obtaining a coagulation time based on the coagulation waveform.

4. The analyzing method, for analyzing a blood specimen, of claim 3, comprising obtaining information concerning an active concentration of fibrinogen based on the coagulation time and one of a calibration curve, a conversion table or a conversion equation defining a correlation of an active concentration of fibrinogen and a coagulation time.

5. An analyzing method for analyzing a blood specimen, the analyzing method comprising:
    mixing a blood specimen and a thrombin-containing reagent to coagulate the blood specimen, and obtaining a coagulation waveform comprised of values of an optical parameter versus time measured on the blood specimen as the blood specimen coagulates after the blood specimen and the thrombin-containing reagent are mixed;
    obtaining, based on the coagulation waveform, a value of a parameter concerning differentiation of the coagulation waveform or a total reaction time that is a length of time beginning from when the blood specimen and the thrombin-containing reagent are mixed and up to a time when a measurement value of the coagulation waveform no longer changes, and a coagulation time, wherein the parameter concerning the differentiation of the coagulation waveform is at least one selected from a maximum coagulation speed (|min 1|) or a maximum coagulation deceleration (|max 2|); and
    obtaining an estimated amount of antigen of fibrinogen in the blood specimen based on the obtained value of the parameter or the total reaction time, using a calibration curve or a regression equation of the calibration curve, wherein the estimated amount of antigen of fibrinogen correlates to an amount of antigen of fibrinogen in the blood specimen obtained by immunological measurement using an anti-fibrinogen antibody, and wherein the calibration curve is created based on plots of the differentiation parameter or total reaction time vs. an amount of antigen of fibrinogen determined by the immunological measurement for a plurality of normal specimens;
    obtaining an active concentration of fibrinogen in the blood specimen based on the coagulation time, using one of a calibration curve, a conversion table or a conversion equation defining a correlation of the active concentration of fibrinogen and a coagulation time; and
    obtaining a quantitative or qualitative information concerning a function of fibrinogen that represents coagulability of fibrinogen in the blood specimen in response to an addition of thrombin, by comparing the estimated amount of antigen of fibrinogen and the active concentration of fibrinogen in the blood specimen.

6. The analyzing method of claim 5, wherein the quantitative information concerning the function of fibrinogen is information concerning a ratio between the estimated amount of antigen of fibrinogen and the active concentration of fibrinogen.

7. The analyzing method of claim 6, further comprising determining whether or not the blood specimen has an abnormality in fibrinogen based on the ratio.

8. The analyzing method of claim 7, wherein the abnormality in fibrinogen is abnormality of an activity of fibrinogen.

9. A blood specimen analyzer comprising:
a measurement unit configured to obtain a coagulation waveform from a prepared measurement sample that contains a blood specimen and a thrombin-containing reagent, wherein the coagulation waveform is comprised of values of an optical parameter versus time measured on the blood specimen as the blood specimen coagulates after the blood specimen and the thrombin-containing reagent are mixed; and
an information obtaining unit configured to obtain a quantitative or qualitative information concerning an estimated amount of antigen of fibrinogen in the blood specimen based on the coagulation waveform, wherein the estimated amount of antigen of fibrinogen correlates to an amount of antigen of fibrinogen in the blood specimen obtained by immunological measurement using an anti-fibrinogen antibody, wherein the information obtaining unit is further configured to:
obtain a value of a parameter concerning differentiation of the coagulation waveform or a total reaction time that is a length of time beginning from when the blood specimen and the thrombin-containing reagent are mixed and up to a time when a measurement value of the coagulation waveform no longer changes based on the coagulation waveform obtained by the measurement unit, wherein the parameter concerning the differentiation of the coagulation waveform is at least one selected from a maximum coagulation speed |min 1| or a maximum coagulation deceleration |max 2|, and
obtain the information concerning the estimated amount of antigen of fibrinogen in the blood specimen based on the obtained value of the parameter or the total reaction time using a calibration curve or a regression equation of the calibration curve, wherein the calibration curve is created based on plots of the differentiation parameter or total reaction time vs. an amount of antigen of fibrinogen determined by the immunological measurement for a plurality of normal specimens.

10. A blood specimen analyzer comprising:
a measurement unit configured to obtain a coagulation waveform from a prepared measurement sample that contains a blood specimen and a thrombin-containing reagent, wherein the coagulation waveform is comprised of values of an optical parameter versus time measured on the blood specimen as the blood specimen coagulates after the blood specimen and the thrombin-containing reagent are mixed; and
an information obtaining unit configured to obtain a quantitative or qualitative information concerning a function of fibrinogen that represents coagulability of fibrinogen in the blood specimen in response to an addition of thrombin by comparing an estimated amount of antigen of fibrinogen and an active concentration of fibrinogen in the blood specimen, wherein the estimated amount of antigen of fibrinogen correlates to an amount of antigen of fibrinogen in the blood specimen obtained by immunological measurement using an anti-fibrinogen antibody, wherein the information obtaining unit is further configured to:
obtain a value of a parameter concerning differentiation of the coagulation waveform or a total reaction time that is a length of time beginning from when the blood specimen and the thrombin-containing reagent are mixed and up to a time when a measurement value of the coagulation waveform no longer changes, and a coagulation time, based on the coagulation waveform obtained by the measurement unit, wherein the parameter concerning the differentiation of the coagulation waveform is at least one selected from a maximum coagulation speed |min 1| or a maximum coagulation deceleration (|max 2|),
obtain the estimated amount of antigen of fibrinogen in the blood specimen based on the obtained value of the parameter or the total reaction time, using a calibration curve or a regression equation of the calibration curve, wherein the calibration curve is created based on plots of the differentiation parameter or total reaction time vs. an amount of antigen of fibrinogen determined by the immunological measurement for a plurality of normal specimens,
obtain the active concentration of fibrinogen in the blood specimen based on the coagulation time, using one of a calibration curve, a conversion table or a conversion equation defining a correlation of an active concentration of fibrinogen and a coagulation time, and
obtain the information concerning the function of fibrinogen by comparing the estimated amount of antigen of fibrinogen and the active concentration of fibrinogen in the blood specimen.

* * * * *